United States Patent
Devaud et al.

(10) Patent No.: US 9,334,489 B2
(45) Date of Patent: May 10, 2016

(54) CHO EXPRESSION SYSTEM

(71) Applicant: SANOFI, Paris (FR)

(72) Inventors: Catherine Devaud, Paris (FR); Bruno Dumas, Paris (FR); Nabil Lounis, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/407,836

(22) PCT Filed: Jun. 14, 2013

(86) PCT No.: PCT/EP2013/062400
§ 371 (c)(1),
(2) Date: May 11, 2015

(87) PCT Pub. No.: WO2013/186371
PCT Pub. Date: Dec. 19, 2013

(65) Prior Publication Data
US 2015/0140607 A1    May 21, 2015

(30) Foreign Application Priority Data
Jun. 14, 2012  (EP) .................................... 12305677

(51) Int. Cl.
| | | |
|---|---|---|
| *C12N 15/85* | (2006.01) | |
| *C12P 21/00* | (2006.01) | |
| *C12N 9/00* | (2006.01) | |
| *C07K 16/00* | (2006.01) | |

(52) U.S. Cl.
CPC . *C12N 9/93* (2013.01); *C07K 16/00* (2013.01); *C12N 15/85* (2013.01); *C07K 2317/14* (2013.01); *C12N 2800/22* (2013.01); *C12N 2820/55* (2013.01); *C12N 2830/60* (2013.01); *C12Y 603/01002* (2013.01)

(58) Field of Classification Search
None
See application file for complete search history.

(56) References Cited

U.S. PATENT DOCUMENTS

| 7,244,616 B2 * | 7/2007 | Chan et al. ............... 435/325 |
| 2010/0221781 A1 * | 9/2010 | Kopetzki et al. ........... 435/69.6 |

FOREIGN PATENT DOCUMENTS

| KR | 100 267 720 B1 | 7/2000 |
| WO | WO 87/04462 A1 | 7/1987 |
| WO | WO 89/01036 A1 | 2/1989 |
| WO | WO 91/06657 A1 | 5/1991 |
| WO | WO 2009/065054 A2 | 5/2009 |

OTHER PUBLICATIONS

Benoist & Chambon, "In vivo sequence requirements of the SV40 early promotor region." Nature 290 (5804):304-10 (Mar. 1981).
Chatellard et al., "The IE2 promoter/enhancer region from mouse CMV provides high levels of therapeutic protein expression in mammalian cells." Biotechnol Bioeng. 96(1):106-17 (Jan. 2007).
Kuo et al., "Mouse glutamine synthetase is encoded by a single gene that can be expressed in a localized fashion", Journal of Molecular Biology, 208(1):45-56 (Jul. 1989).
Moreau et al., "The SV40 72 base repair repeat has a striking effect on gene expression both in SV40 and other chimeric recombinants." Nucleic Acids Res. 9(22):6047-68 (Nov. 1981).
Needleman & Wunsch, "A general method applicable to the search for similarities in the amino acid sequence of two proteins." J. Mol. Biol. 48(3):443-53 (Mar. 1970).
Omasa et al., "Expression and amplification of glutamine synthetase gene endows HepG2 cells with ammonia-metabolizing activity for bioartificial liver support system", Enzyme and Microbial Technology, 35(6-7):519-24 (Dec. 2004).
Pu et al., "Rapid establishment of high-producing cell lines using dicistronic vectors with glutamine synthetase as the selection marker." Mol Biotechol. 10(1):17-25 (Aug. 1998).
Raab et al., "The GeneOptimizer Algorithm: using a sliding window approach to cope with the vast sequence space in multiparameter DNA sequence optimization." Syst Synth Biol. 4(3):215-25 (Sep. 2010).
Teschendorf et al., "Comparison of the EF-1 alpha and the CMV promoter for engineering stable tumor cell lines using recombinant adeno-associated virus." Anticancer Res. 22(6A):3325-30 (Nov.-Dec. 2002).
The European Search Report for European Application No. EP 12 30 5677, dated Nov. 16, 2012, pp. 1-3.
The International Search Report of the International Searching Authority for International Application No. PCT/EP2013/062400, dated Jul. 30, 2013, pp. 1-5.

* cited by examiner

*Primary Examiner* — Celine Qian
(74) *Attorney, Agent, or Firm* — McDonnell Boehnen Hulbert & Berghoff LLP

(57) ABSTRACT

The present invention is within the field of industrial protein production. The inventors have designed and constructed a new expression system comprising an expression vector coding for a glutamine synthetase of human or dog origin, and a CHO cell line. More specifically, the invention pertains to a combination of (i) a DNA vector suitable for production of a recombinant protein, wherein said vector comprises a sequence coding for a glutamine synthetase, and (ii) a Chinese Hamster Ovary (CHO) cell line, wherein said GS comprises a sequence at least 94.5% identical to the sequence of SEQ ID NO: 1 or to the sequence of SEQ ID NO: 2.

16 Claims, 6 Drawing Sheets

```
SEQ ID NO:1 Human    MTTSASSHLNKGIKQVYMSLPQGEKVQAMYIWIDGTGEGLRCKTRTLDSEPKCVEELPEW  60
SEQ ID NO:2 Dog      MATSASSHLNKGIKQVYMSLPQGEKVQAMYIWIDGTGEGLRCKTRTLDSEPKGVEELPEW  60
SEQ ID NO:3 CHO      MATSASSHLNKNIKQMYICLPQGEKVQAMYIWVDGTGEGLRCKTRTLDCEPKCVEELPEW  60
                     *:********* ***:** : ******************:*******: ***.******

SEQ ID NO:1 Human    NFDGSSTLQSEGSNSDMYLVPAAMFRDPFRKDPNKLVLCEVFKYNRRPAEINLRHTCKRI 120
SEQ ID NO:2 Dog      NFDGSSTFQSEGSNSDMYLVPAAMFRDPFRKDPNKLVFCEVFKYNRKPAEINLRHTCKRI 120
SEQ ID NO:3 CHO      NFDGSSTFQSEGSNSDMYLSPVAMFRDPFRRDPNKLVFCEVFKYNRKPAEINLRHSCKRI 120
                     *******:*********** .:******** :*****:*******:*******:****

SEQ ID NO:1 Human    MDMVSNQHPWFGMEQEYTLMGTDGHPFGWPSNGFPGPQGPYYCGVGADRAYGRDIVEAHY 180
SEQ ID NO:2 Dog      MDMVSNQHPWFGMEQEYTLMGTDGHPFGWPSNGFPGPQGPYYCGVGADKAYGRDIVEAHY 180
SEQ ID NO:3 CHO      MDMVSNQHPWFGMEQEYTLMGTDGHPFGWPSNGFPGPQGPYYCGVGADKAYGRDIVEAHY 180
                     ***********************************************:***********

SEQ ID NO:1 Human    RACLYAGVKIAGTNAEVMPAQWEFQIGPCEGISMGDHLWVARFILHRVCEDFGVIATFDP 240
SEQ ID NO:2 Dog      RACLYAGIKIAGTNAEVMPAQWEFQIGPCEGIDMGDHLWVARFILHRVCEDFGVIATFDP 240
SEQ ID NO:3 CHO      RACLYAGVKITGTNAEVMPAQWEFQIGPCEGIRMGDHLWVARFILHRVCEDFGVIATFDP 240
                     *******:**:******************** **************************

SEQ ID NO:1 Human    KPIPGNWNGAGCHTNFSTKAMREENGLKYIEEAIEKLSKRHQYHIRAYDPKGLDNARRL 300
SEQ ID NO:2 Dog      KPIPGNWNGAGCHTNFSTKAMREENGLKYIEESIEKLSKRHQYHIRAYDPKGLDNARRL 300
SEQ ID NO:3 CHO      KPIPGNWNGAGCHTNFSTKAMREENGLKHIEEAIEKLSKRHYHIRAYDPKGLDNARRL 300
                     ****************************:***:*******:*****************

SEQ ID NO:1 Human    TGFHETSNINDFSAGVANRSASIRIPRTVGQEKKGYFEDRRPSANCDPFSVTEALIRTCL 360
SEQ ID NO:2 Dog      TGFHETSNINDFSAGVANRSASIRIPRTVGQEKKGYFEDRRPSANCDPFSVTEALIRTCL 360
SEQ ID NO:3 CHO      TGFHETSNINDFSAGVANRSASIRIPRTVGQEKKGYFEDRRPSANCDPFAVTEAIVRTCL 360
                     *************************************************:****:.****

SEQ ID NO:1 Human    LNETGDEPFQYKN 373
SEQ ID NO:2 Dog      LNETGDEPFQYKN 373
SEQ ID NO:3 CHO      LNETGDEPFQYKN 373
                     *************
```

CHO EXPRESSION SYSTEM

This application is a national stage application under 35 U.S.C. §371 of International application Ser. No. PCT/EP2013/062400, filed Jun. 14, 2013, which claims the benefit of EP Application Ser. No. 12305677.2, filed Jun. 14, 2012, the disclosures of each of which are explicitly incorporated by reference herein.

FIELD OF THE INVENTION

The present invention is within the field of industrial protein production. The inventors have designed and constructed a new expression system comprising an expression vector coding for a glutamine synthetase of human or of dog origin, and a CHO cell line.

More specifically, the invention pertains to a combination of (i) a DNA vector suitable for production of a recombinant protein, wherein said vector comprises a sequence coding for a glutamine synthetase, and (ii) a Chinese Hamster Ovary (CHO) cell line, wherein said GS comprises a sequence at least 94.5% identical to the sequence of SEQ ID NO: 1 or to the sequence of SEQ ID NO: 2.

BACKGROUND OF THE INVENTION

When producing recombinant proteins at industrial scale, one must isolate clones producing high amounts of recombinant proteins.

Introducing heterologous genes into animal host cells and screening for expression of the added genes is a lengthy and complicated process. The process involves the transfection and the selection of clones with stable long-term expression, and the screening for high expression rates of the recombinant protein.

When generating clones expressing a recombinant protein from expression vectors, host cells are usually transfected with a DNA vector encoding both the protein of interest and the selection marker on the same vector. Such an expression vector thus comprises a selectable marker allowing the selection of clones in which the expression vector is present. Such a selectable marker may also lead to a co-amplification taking place, thereby allowing the isolation of high-producer clones.

Several such selectable markers are known in the art, including e.g. G418, hygromycin, puromycin, zeomycin, dihydrofolate reductase (DHFR), glutamine synthetase (GS) and hypoxanthine-guanine phosphoribosyltransferase (HPRT). In particular, GS is widely used as a selectable marker in the field of industrial recombinant protein production in eukaryotic cells.

More specifically, WO 87/04462 describes the use of glutamine synthetase (GS) as a selectable marker. The examples teach an expression vector comprising, as a selectable marker, the sequence coding for a GS of Chinese hamster origin. It is further shown that such an expression vector allows production of a recombinant protein upon transfection of the expression vector into CHO cells, the recombinant protein being tPA.

Even though the above CHO expression system based on the use of GS as a selectable marker was described as early as in the 80'ies, it remains a standard in the art still today. In particular, no significant improvement to the original GS selectable marker has been published.

Indeed, the Korean patent KR10-0267720 discloses the use of human GS as a selectable marker. However, the exact sequence of the human GS used is not disclosed. Moreover, it is also indicated the technical effect (high yield) is only linked both with the human GS and with the specific SV40 promoter that is used (i.e. an SV40 promoter that lacks positions 128 to 270).

There is thus a need in the art for additional and/or improved expression systems allowing the isolation of a high number of clones expressing the recombinant protein for which production is desired, at least some of these clones exhibiting high expression rates of the recombinant protein.

SUMMARY OF THE INVENTION

The inventors have surprisingly found that when producing recombinant proteins in CHO cells, the use of a GS of human or of dog origin yields better results than the use of a GS of CHO origin (see e.g. FIGS. 2 and 3).

In particular, it has been found that the use of a GS of human origin is especially advantageous since it allows the isolation of more clones expressing the recombinant proteins than when a GS of CHO origin is used, some of them expressing the recombinant protein at higher levels than when a GS of CHO origin is used (see e.g. FIG. 3).

One embodiment of the invention provides a Chinese Hamster Ovary (CHO) cell line comprising a deoxyribonucleic acid (DNA) expression vector, and wherein the vector comprises a nucleotide sequence coding for a heterologous mammalian glutamine synthetase (GS) and at least one expression cassette for expressing a recombinant protein, wherein the GS comprises a protein sequence that is at least 94.5% identical to the sequence of SEQ ID NO: 1 or to the sequence of SEQ ID NO: 2; or a protein fragment of at least 100 consecutive amino acids of SEQ ID NO: 1 or SEQ ID NO: 2. In another embodiment of the invention, the GS comprises a sequence at least 94.5% identical to the sequence of SEQ ID NO: 1 and to the sequence of SEQ ID NO: 2. In another embodiment of the invention, the GS comprises a sequence at least 97.5% identical to the sequence of SEQ ID NO: 1. In a particular embodiment of the invention, the GS is a human GS and comprises a sequence of SEQ ID NO: 1. In another embodiment of the invention, the GS is a dog GS and has a sequence of SEQ ID NO: 2.

In still another embodiment of the invention the CHO cell line comprises a deoxyribonucleic acid (DNA) expression vector, and the vector comprises a nucleotide sequence coding for a heterologous mammalian glutamine synthetase (GS) and at least one expression cassette for expressing a recombinant protein, wherein the triplet codons of said sequence coding for a GS have been biased for expression in CHO cells. In another embodiment of the invention, said sequence coding for a GS comprises a sequence at least 80% identical to the sequence of SEQ ID NO: 8 or SEQ ID NO: 9. In a particular embodiment of the invention, the sequence coding for a GS comprises a sequence of SEQ ID NO: 8 or SEQ ID NO: 9. In another embodiment of the invention, the sequence coding for human GS is placed under the control of a Simian vacuolating virus 40 (SV40) promoter and the recombinant protein is a monoclonal antibody.

In still another embodiment of the invention the CHO cell line comprises a deoxyribonucleic acid (DNA) expression vector, and the vector comprises a nucleotide sequence coding for a heterologous mammalian glutamine synthetase (GS) and at least one expression cassette for expressing a recombinant protein wherein the triplet codons of said sequence coding for a GS have been biased for expression in CHO cells. In another embodiment, the vector comprises a first expression cassette suitable for cloning of an antibody light chain, and a second expression cassette suitable for cloning of an antibody heavy chain. In yet another embodiment, the first and second expression cassettes each comprise a CMV promoter and the CHO cell line is capable of growing in serum-free medium or serum free and animal derived protein free medium.

In one embodiment of the invention, the CHO cell line is the cell line deposited under No. CCL-61 at the ATCC or is derived from the cell line deposited under No. CCL-61 at the ATCC. In another embodiment of the invention, the CHO cell line allows for obtaining clones producing at least 1 mg/L of recombinant protein upon transfection of said vector into the CHO cell line deposited under No. CCL-61 at the ATCC.

In still another embodiment of the invention, the CHO cell line comprises a deoxyribonucleic acid (DNA) expression vector, and the vector comprises a glutamine synthase (GS) nucleotide sequence (i.e. a nucleotide sequence coding for a glutamine synthetase (GS)) and at least one expression cassette for expressing a recombinant protein. In one embodiment, the vector does not contain a heterologous gene for expression of a recombinant protein. In another embodiment of the invention, the vector contains at least one sequence coding for a recombinant protein. In another embodiment, the vector contains a heterologous gene encoding a recombinant protein that is a monoclonal antibody. In another embodiment of the invention, the vector contains a heterologous gene encoding a recombinant protein that is an immunogenic protein for inducing an antibody response. In another embodiment of the invention, the vector contains a heterologous gene encoding a recombinant protein that is an enzyme for enzyme replacement therapy or for industrial use.

One embodiment of the invention provides a deoxyribonucleic acid (DNA) expression vector, and the vector comprises a nucleotide sequence coding for a glutamine synthetase (GS) under the control of a Simian vacuolating virus 40 (SV40) promoter and a first expression cassette suitable for cloning of a heterologous recombinant protein under the control of a CMV promoter. In a particular embodiment of the invention, the GS comprises a protein sequence that is at least 94.5% identical to the sequence of SEQ ID NO: 1 or to the sequence of SEQ ID NO: 2; or a fragment of at least 100 consecutive amino acids of SEQ ID NO: 1 or SEQ ID NO: 2.

Another embodiment of the invention provides a deoxyribonucleic acid (DNA) expression vector, and the vector comprises a nucleotide sequence coding for a glutamine synthetase (GS) under the control of a Simian vacuolating virus 40 (SV40) promoter and a first expression cassette suitable for cloning of an antibody light chain under the control of a CMV promoter, and a second expression cassette suitable for cloning of an antibody heavy chain under the control of a CMV promoter. In a particular embodiment of the invention, the GS comprises a protein sequence that is least 94.5% identical to the sequence of SEQ ID NO: 1 or to the sequence of SEQ ID NO: 2 or a fragment of at least 100 consecutive amino acids of SEQ ID NO: 1 or SEQ ID NO: 2.

One embodiment of the invention provides a vector as defined in FIG. 1.

One embodiment of the invention provides an in vitro method of producing a recombinant protein comprising the steps of providing a CHO cell line; culturing the CHO cell line obtained under conditions suitable for production of the recombinant protein; and isolating and/or purifying said recombinant protein. Another embodiment provides a further step of formulating the recombinant protein into a pharmaceutical composition.

One embodiment of the invention pertains to a combination of:
i) a eukaryotic cell line (e.g. a Chinese Hamster Ovary (CHO) cell line); and
ii) a DNA vector suitable for production of a recombinant protein, wherein said vector comprises a sequence coding for a heterologous mammalian glutamine synthetase (GS) (e.g. a GS comprising a sequence at least 94.5% identical to the sequence of SEQ ID NO: 1 or to the sequence of SEQ ID NO: 2).

Another aspect of the present invention is directed to a kit comprising the above combination.

Still another aspect of the invention is directed to the DNA vector as such.

Still another aspect of the invention is directed to a CHO cell line comprising the DNA vector.

In still another aspect, the invention pertains to an in vitro method of producing a recombinant protein comprising the steps of:
a) providing a vector as defined hereabove;
b) transfecting a cell line with said vector;
c) culturing the transfected cell line obtained at step (b) under conditions suitable for production of the recombinant protein; and
d) isolating and/or purifying said recombinant protein.

Still another aspect of the invention pertains to the use of such a combination, or of such a vector, or of such cell line, for producing a recombinant protein in vitro.

BRIEF DESCRIPTION OF THE FIGURES

FIG. 5 shows a sequence alignment between the human GS of SEQ ID NO: 1, the dog GS of SEQ ID NO: 2, and the CHO GS of SEQ ID NO: 3, which was made using the "CLUSTAL 2.1 multiple sequence alignment" program. Residues that are different in human and in dog GS, as compared with CHO GS, are indicated with a black arrows. These residues correspond to residues 12, 16, 18, 19, 33, 49, 80, 82, 91, 116, 191, 269, 282, 350, 355 and 356 of SEQ ID NO: 1 and of SEQ ID NO: 2 (the amino acid variations corresponding to 12G, 16V, 18M, 19S, 33I, 49S, 80V, 82A, 91K, 116T, 191A, 269Y, 282Q, 350S, 355L and 356I, respectively). Residues that are different in human GS, as compared to dog and CHO GS, are indicated with a grey arrow. These residues correspond to residues at position 2, 68, 98, 107, 169, 213 of SEQ ID NO: 1 (the amino acid variations corresponding to 2T, 68L, 98L, 107R, 169R and 213S, respectively).

DETAILED DESCRIPTION OF THE INVENTION

Figure 1:
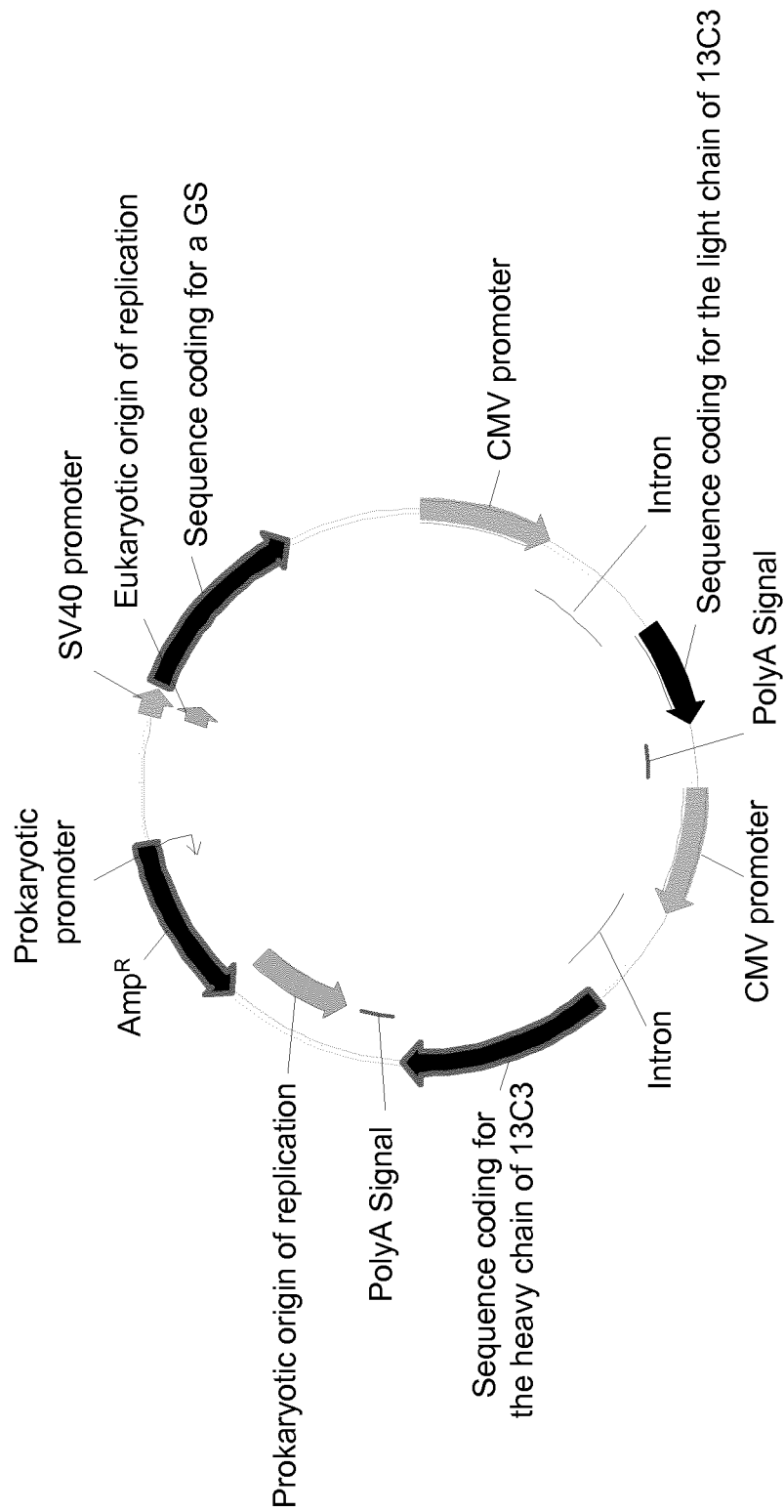
FIG. 1 shows a scheme of the vectors used in the Examples (pBH3695, pBH3700, pBH3694, pBH3699, pBH3698, pBH3697 and pBH3623).

Another aspect of the invention is directed to a combination of:
i) a eukaryotic cell line; and
ii) a DNA (deoxyribonucleic acid) vector suitable for production of a recombinant protein, wherein said vector comprises a sequence coding for a hererologous mammalian glutamine synthetase (GS).

The eukaryotic cell line may for instance be a yeast cell line (e.g. a *Saccharomyces cerevisiae* or a *Yarrowia lipolytica* cell line), a fungal cell line (e.g. an *Aspergillus niger* cell line), an insect cell line or a mammalian cell line (including but not limited to CHO cell lines, human cell lines such as HEK293 or PERC.6, mouse cell lines such as NS0, and monkey cell lines). In a specific embodiment, the eukaryotic cell line is a CHO cell line. The GS encoded by the DNA vector originates from a heterologous mammalian species, and may for instance originate from human or dog.

In a specific embodiment, said heterologous mammalian GS comprises or consists of a sequence:
at least 94.5% identical to at least one of SEQ ID NO: 1 or SEQ ID NO: 2, and/or
consisting of a fragment of at least 100, 150, 200, 250, 300 or 350 consecutive amino acids of SEQ ID NO: 1 or SEQ ID NO: 2.

Such a combination, further referred to as "combination according to the invention", constitutes an expression system.

More specifically, one aspect of the invention is directed to a combination of:
i) a DNA vector suitable for production of a recombinant protein, wherein said vector comprises a sequence coding for a glutamine synthetase (GS); and
ii) a Chinese Hamster Ovary (CHO) cell line;
wherein said GS comprises a sequence:
at least 94.5% identical to the sequence of SEQ ID NO: 1 or to the sequence of SEQ ID NO: 2; or
consisting of a fragment of at least 100, 150, 200, 250, 300 or 350 consecutive amino acids of SEQ ID NO: 1 or SEQ ID NO: 2.

The combination according to the invention may for example be provided under the form of a kit, e.g. with one vial comprising the DNA vector, and another vial comprising the cell line.

When the expression system is used for producing a recombinant protein, the vector is introduced into the cell line (it may for example be stably or transiently transfected into the cell line).

The present invention thus encompasses:
a combination wherein the vector is present within the cell line on the one hand, and
a combination wherein the vector is isolated from the cell line on the other hand.

1. Vector According to the Invention

The DNA vector for use in the combination according to the invention (further referred to as "vector according to the invention") is suitable for the production of a recombinant protein, and comprises a sequence coding for a glutamine synthetase (GS).

As used herein, the term "glutamine synthetase" or "GS" refers to a polypeptide capable of catalyzing the condensation of glutamate and ammonia to form glutamine, as represented by the following biochemical reaction:

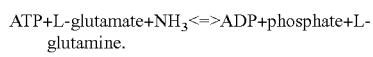
ATP+L-glutamate+NH$_3$<=>ADP+phosphate+L-glutamine.

Such a polypeptide is classified under Enzyme Commission (EC) number 6.3.1.2. Polypeptides capable of catalyzing the above reaction exhibit "GS ctivity".

The GS that is used in the frame of the present invention (further referred to as "GS according to the invention") may comprise or consist of a sequence at least 94.5%, 95%, 95.5%, 96%, 96.5%, 97%, 97.5%, 98%, 98.5%, 99%, 99.5% A or 100% identical to at least one of SEQ ID NO: 1 or SEQ ID NO: 2. Indeed, it has been found that such a GS is advantageous for use as a selectable marker in CHO cells (see Example 1). It may also comprise or consist of a fragment of at least 100, 150, 200, 250, 300 or 350 consecutive amino acids of SEQ ID NO: 1 or SEQ ID NO: 2, provided the protein retains its GS activity.

In a specific embodiment, the GS according to the invention comprises or consists of a sequence at least 94.5%, 95%, 95.5%, 96%, 96.5%, 97%, 97.5%, 98%, 98.5%, 99%, 99.5% or 100% identical both to the sequence of SEQ ID NO: 1 and to the sequence of SEQ ID NO: 2.

In a specific embodiment, the GS according to the invention comprises or consists of a sequence at least 97.5%, 98%, 98.5%, 99%, 99.5% or 100% identical to the sequence of SEQ ID NO: 1. Such a GS is particularly advantageous for use as a selectable marker in CHO cells (see Example 1), in particular in the E94 CHO cell line (see Example 2).

In a specific embodiment, the GS according to the invention is a human GS, i.e., a GS of human origin. As used herein, the term "human GS" refers to a sequence comprising or consisting of SEQ ID NO: 1, as well as variants thereof exhibiting GS activity. Such variants may for example correspond to variants that occur naturally in human species (such as allelic variants or splice variants). Alternatively, such variants may correspond to variants obtained by genetic engineering. Most preferably, such variants only differ from the sequence of SEQ ID NO: 1 by the presence of at most 22, 20, 15, 10, 9, 8, 7, 6, 5, 4, 3, 2 or 1 amino acid variations as compared to SEQ ID NO: 1 (said variations including substitutions, insertions and deletions).

In another specific embodiment, the GS according to the invention is a dog GS, i.e., a GS of dog origin. As used herein, the term "dog GS" refers to a sequence comprising or consisting of SEQ ID NO: 2, as well as variants thereof exhibiting GS activity. Such variants may for example correspond to variants that occur naturally in dog species (such as allelic variants or splice variants). Alternatively, such variants may correspond to variants obtained by genetic engineering. Most preferably, such variants only differ from the sequence of SEQ ID NO: 2 by the presence of at most 22, 20, 15, 10, 9, 8, 7, 6, 5, 4, 3, 2 or 1 amino acid variations as compared to SEQ ID NO: 2 (said variations including substitutions, insertions and deletions).

In a specific embodiment, the GS according to the invention comprises at least 1, 2, 3, 4, 5, 6, 10, 15, 16, 20 or 22 of the following amino acids: 12G, 16V, 18M, 19S, 33I, 49S, 80V, 82A, 91K, 116T, 191A, 269Y, 282Q, 350S, 355L, 356I, 2T, 68L, 98L, 107R, 169R and 213S, wherein the number indicates the position on SEQ ID NO: 1 and SEQ ID NO: 2, and the letter the nature of the amino acid (using the one-letter genetic code). In a more specific embodiment, the GS according to the invention comprises at least 1, 2, 3, 4, 5 or 6 of the following amino acids: 2T, 68L, 98L, 107R, 169R and 213S. In another more specific embodiment, the GS according to the invention comprises at least 1, 2, 3, 4, 5, 6, 10, 15 or 16 of the following amino acids: 12G, 16V, 18M, 19S, 33I, 49S, 80V, 82A, 91K, 116T, 191A, 269Y, 282Q, 350S, 355L and 356I. The above amino acids appear to be specific to the human and/or dog GS, as compared to the CHO GS (see FIG. 5).

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

In the frame of the present application, the percentage of identity is calculated using a global alignment (i.e., the two sequences are compared over their entire length).

Methods for comparing the identity and homology of two or more sequences are well known in the art. The <<needle>> program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used when performing a global alignment. This needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

Variants of a reference sequence may comprise mutations such as deletions, insertions and/or substitutions compared to the reference sequence. In case of substitutions, the substitution preferably corresponds to a conservative substitution as indicated in the table below.

| Conservative substitutions | Type of Amino Acid |
| --- | --- |
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

The DNA vector according to the invention comprises a sequence coding for such a GS according to the invention. The sequence coding for such a GS according to the invention may be the naturally-occurring nucleotide sequence. Alternatively, the triplet codons of the sequence coding for such a GS may be biased for expression in CHO cells. Software and algorithms for biasing sequence in order to obtain an optimal expression are known in the art and include, e.g., the algorithm described in Raab et al. (2010, Syst Synth Biol. 4:215-25). This algorithm not only provides the best available codons for expression, but also takes into account the GC content and the absence of non desired DNA motifs.

For instance, the sequence coding for the GS according to the invention may comprise or consist of a sequence at least 80%, 81%, 82%, 83%, 84%, 85%, 86%, 87%, 88%, 89%, 90%, 91%, 92%, 93%, 94%, 95%, 96%, 97%, 98%, 99% or 100% to the sequence of SEQ ID NO: 8 (i.e. a sequence coding for the human GS of SEQ ID NO: 1, which has been designed for optimal expression in CHO cells) and/or to the sequence of SEQ ID NO: 9 (i.e. a sequence coding for a dog GS of SEQ ID NO: 2, which has been designed for optimal expression in CHO cells).

In a specific embodiment, the sequence coding for the GS according to the invention comprises or consists of a sequence of SEQ ID NO: 8 or SEQ ID NO: 9.

On the DNA vector according to the invention, the sequence coding for the GS according to the invention may be placed under the control of any promoter known to those skilled in the art.

For instance, the sequence coding for the GS according to the invention may for example be placed under the control of a Simian vacuolating virus 40 (SV40) promoter, for instance the late or the early promoter of SV40. An early SV40 promoter is for example described in Benoist and Chambon (1981, Nature. 290:304-10) and in Moreau et al. (1981, Nucleic Acids Res. 9:6047-68). In particular, said SV40 promoter is a full-length promoter. Said SV40 promoter may also have a replication origin containing a 72 bp repeat.

In a specific embodiment, said SV40 promoter is not an SV40 promoter in which positions 128 to 270 have been removed, i.e. said SV40 promoter is not the SV40 promoter described in Korean patent No. 10-0267720 and transforming the E. coli transformant deposited to the Gene Bank, Institute of Bioengineering, KIST on 17 Dec. 1997 under the Deposition Number: KCTC 8860 P.

In another specific embodiment, the sequence coding for the GS according to the invention is not placed under the control of a SV40 promoter.

DNA vectors that are suitable for the production of recombinant proteins are known to those skilled in the art. Such DNA vectors typically correspond to expression vectors that comprise an origin of replication and at least one expression cassette allowing the cloning and the expression of the recombinant protein for which production is desired. An expression cassette typically comprises a 5' untranslated region (comprising or consisting of a promoter, and optionally an enhancer sequence), one or more restriction sites allowing the cloning of a sequence coding for the recombinant protein, a 3' untranslated region (e.g. a polyA signal), and optionally one or more introns. The promoter sequence may correspond to any strong promoter well-known to the art, such as e.g. the human CMV promoter. The vector according to the invention may for instance have the structure depicted on FIG. 1, which is explained in more details in Example 1, provided that the heavy chain and the light chain of 13C3 may be replaced with two other coding sequences (e.g. sequences coding for the heavy chain and the light chain of another antibody).

The recombinant protein may correspond to any protein that is of interest to those skilled in the art. As used herein, the term "protein" is meant to encompass peptides (i.e. amino acid chains of less than 50 amino acids), polypeptides (i.e. amino acid chains of at least 50 amino acids), monomeric proteins (i.e. proteins consisting of one amino acid chain) and multimeric proteins (i.e. proteins consisting of two or more amino acid chains, such as e.g. monoclonal antibodies).

The vector according to the invention typically comprises a number of expression cassettes that is identical to the number of different amino acid chains that constitute the protein (e.g. one expression cassette in case of a monomeric protein or homodimeric protein, two in the case of a heterodimeric protein or of a monoclonal antibody, etc.).

Alternatively, the DNA vector according to the invention may comprise only one expression cassette even when production of a heterodimeric protein or of a monoclonal antibody is desired. In such a case, the sequence(s) coding for the other amino acid chain(s) of the protein is (are) present on an expression separate vector, which is co-transfected with the vector according to the invention into the CHO cell line.

In a specific embodiment, the DNA vector according to the invention may be devoid of expression cassette. In such a case, the expression cassette(s) suitable for expression of the recombinant protein is (are) present on a separate vector, which is co-transfected with the vector according to the invention into the CHO cell line.

Throughout the present specification, the term "recombinant protein" refers to any recombinant protein for which production is desired. It can for example correspond to a therapeutic and/or a prophylactic protein, i.e. a protein intended for use as a medicament (including vaccines). In a specific embodiment, the recombinant protein for which production is desired is not a glutamine synthetase (GS). In another specific embodiment, the recombinant protein for which production is desired is an antibody, for instance a monoclonal antibody. In still another specific embodiment, the recombinant protein for which production is desired is an antigenic protein. In still another specific embodiment, the recombinant protein for which production is desired is not erythropoietin (EPO).

The term "antibody" is used herein in the broadest sense and specifically covers monoclonal antibodies (including full length monoclonal antibodies) of any isotype such as IgG, IgM, IgA, IgD, and IgE, polyclonal antibodies, multispecific antibodies (including bispecific antibodies), antibody fragments (such as e.g. Fv, scFv, dsFv, Fab, Fab', or F(ab')2 fragments), and fusion proteins comprising an antibody fragment. An antibody reactive with a specific antigen can be generated by recombinant methods such as selection of libraries of recombinant antibodies in phage or similar vectors, or by immunizing an animal with the antigen or an antigen-encoding nucleic acid.

A "monoclonal antibody", as used herein, is an antibody obtained from a population of substantially homogeneous antibodies, i.e. the antibodies forming this population are essentially identical except for possible naturally occurring mutations which might be present in minor amounts. These antibodies are directed against a single epitope (or a single group of epitopes in the case of multispecific monoclonal antibodies) and are therefore highly specific.

A typical monoclonal antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus (see Kabat et al., Sequences of Proteins of Immunological Interest, 5th edition, National Institute of Health, Bethesda, Md., 1991). The more highly conserved portions of the variable regions are called the "framework regions".

The monoclonal antibody may for example be a murine antibody, a chimeric antibody, a humanized antibody, or a fully human antibody.

When the recombinant protein for which production is desired is a monoclonal antibody, the vector according to the invention may comprise a first expression cassette suitable for cloning of the antibody light chain, and a second expression cassette suitable for cloning of the antibody heavy chain.

In a specific embodiment, said first and second expression cassettes each comprise the cytomegalovirus (CMV) promoter, for instance a CMV promoter from a human or a murine CMV. More specifically, said first and second expression cassettes may comprise:

- a CMV immediate early enhancer promoter (e.g. the one having the sequence described in Teschendorf et al., 2002, Anticancer Res. 22:3325-30); or
- a IE2 promoter/enhancer region from mouse CMV (e.g. the one having the sequence described in Chatellard et al., 2007, Biotechnol Bioeng. 96:106-17); or
- a hCMV-MIE regulatory element (e.g. the one having the sequence described in WO 89/01036).

The term "antigenic protein" is used herein in the broadest sense and covers any protein capable of generating an immune response, either alone or in combination with an adjuvant. It may be intended for use either in a prophylactic vaccine or in a therapeutic vaccine. In a specific embodiment the antigenic protein is a vaccinal protein, i.e. a protein intended for use in a prophylactic vaccine.

In the frame of the present invention, the DNA vector might either comprise at least one sequence coding for the recombinant protein of interest (e.g. one sequence coding for a monomeric protein, one sequence coding for an antibody chain, or two sequences, coding for an antibody light chain and an antibody heavy chain, respectively), or it might be empty (i.e. devoid of such a sequence coding for the recombinant protein of interest).

In one aspect, the invention is directed to the vector according to the invention per se. Such a vector is preferably intended for use in a CHO cell line. However, it may also be used for expressing proteins in other eukaryotic cell lines such as yeast, fungal, insect or mammalian (e.g. human, mouse, monkey, etc.) cell lines.

2. Cell Line According to the Invention

The cell line for use in the combination according to the invention (further referred to as "cell line according to the invention") is a eukaryotic cell line, e.g. a mammalian cell line such as a CHO cell line. CHO cell lines are commonly used for industrial protein production, and many CHO cell lines are known to those skilled in the art. For instance, such CHO cell lines include, e.g., the CHO-$K_1$ cell line (ATCC Number: CCL-61), the CHO DP-12 cell line (ATCC Nos. CRL-12444 and 12445) and the CHO 1-15 cell line (ATCC Number CRL-9606). These strains are publically available from the American Type Culture Collection.

In a specific embodiment, the CHO cell line according to the invention is capable of growing in serum-free medium (e.g. a chemically-defined medium) and/or in suspension. Such a cell line can easily be obtained by those skilled in the art by adapting the parent cell line to grow in serum-free medium and/or in suspension (e.g. through single cell cloning, through progressive adaptation and/or through a "starve and save" process).

The CHO cell line according to the invention may either be a GS deficient cell line, or a cell line comprising an endogenous GS gene coding for an endogenous GS polypeptide.

In a specific embodiment, the CHO cell line is the cell line deposited under No. CCL-61 at the ATCC. As used herein, the term 'cell line deposited under No. CCL-61 at the ATCC" encompasses the parental clone actually deposited at the ATCC on the one hand, and clones derived therefrom, for instance through single cell cloning, progressive adaptation and/or through a "starve and save" process, on the other hand. More specifically, the cell line deposited under No. CCL-61 at the ATCC can be used to obtain clones capable of growing in serum-free medium and/or in suspension.

In a specific embodiment, the combination according to the invention is characterized in that it allows obtaining clones producing at least 1, 2, 3, 4 or 5 mg/L of recombinant protein upon transfection of the vector into the cell line deposited under No. CCL-61 at the ATCC.

In another aspect, the invention is directed to a CHO cell line comprising a vector according to the invention. Preferably, said CHO cell line is transfected (stably or transiently transfected) with said vector. Most preferably said CHO cell line comprises said vector integrated in its genome.

More specifically, the invention is directed to CHO cell line comprising a DNA expression vector, and wherein said vector comprises a nucleotide sequence coding for a heterologous mammalian glutamine synthetase (GS) and at least one expression cassette for expressing a recombinant protein, wherein said GS comprises a protein sequence:
 a) at least 94.5% identical to the sequence of SEQ ID NO: 1 or to the sequence of SEQ ID NO: 2; or
 b) consisting of a fragment of at least 100 consecutive amino acids of SEQ ID NO: 1 or SEQ ID NO: 2.

3. Kits, Methods and Uses According to the Invention

One aspect of the invention pertains to a kit comprising or consisting of a combination according to the invention. In such a kit, the vector is preferably empty, since this allows the cloning of the protein of interest for those skilled in the art. In addition, the DNA vector is preferably isolated from the cell line in such a kit. The kit may further comprise media suitable for cultivation of the cell line, media suitable for transfection of the vector into the cell line, and/or instructions for use of the expression system.

Another aspect of the invention pertains to the use of the combination according to the invention, or of the vector according to the invention, or of the cell line according to the invention, for producing a recombinant protein in vitro.

Still another aspect of the invention pertains to an in vitro method of producing a recombinant protein, said method comprising or consisting of the following steps:
 a) providing a combination according to the invention;
 b) transfecting said cell line with said DNA vector;
 c) culturing the transfected cell line obtained at step (b) under conditions suitable for production of the recombinant protein; and
 d) isolating and/or purifying said recombinant protein.

As immediately apparent to those skilled in the art, the above aspect relates to a combination according to the invention wherein the DNA vector is isolated from the cell line at step (a).

Still another aspect of the invention pertains to an in vitro method of producing a recombinant protein, said method comprising or consisting of the following steps:
 a) providing a combination according to the invention;
 b) culturing the transfected cell line under conditions suitable for production of the recombinant protein; and
 c) isolating and/or purifying said recombinant protein.

As immediately apparent to those skilled in the art, the above aspect relates to a combination according to the invention wherein the cell line comprises the DNA vector (e.g. the cell line has previously been transected with the DNA vector) at step (a).

Yet another aspect of the invention pertains to an in vitro method of producing a recombinant protein, comprising or consisting of the following steps:
 a) providing a vector according to the invention, wherein said vector comprises at least one sequence coding for a recombinant protein;
 b) transfecting a cell line according to the invention with said vector;
 c) culturing the transfected cell line obtained at step (b) under conditions suitable for production of the recombinant protein; and
 d) isolating and/or purifying said recombinant protein.

Conditions suitable for production of recombinant proteins are well-known to those skilled in the art. The protocols described in the Examples may for instance be used.

In a specific embodiment, a GS inhibitor such as methionine sulphoximine (msx) or phosphinothricin is added when culturing the cell line according to the invention. In a more specific embodiment, increasing concentrations of such a GS inhibitor are added when culturing the cell line. This allows selecting clones in which the vector-derived GS gene (and thus the sequence coding for the recombinant protein) has been amplified.

The above methods may further comprise the step of formulating the recombinant protein into a pharmaceutical composition.

Still another aspect of the invention is directed to a method for co-amplifying a recombinant DNA sequence which encodes a recombinant protein, comprising or consisting of the following steps:
 a) providing a vector according to the invention, wherein said vector comprises a sequence which encodes said recombinant protein;
 b) providing a cell line according to the invention;
 c) transfecting said cell line with said vector; and
 d) culturing said transfected cell line under conditions which allow transformants containing an amplified number of copies of a vector-derived sequence which encodes GS to be selected, wherein said transformants also contain an amplified number of copies of the sequence which encodes the complete amino acid sequence of the recombinant protein.

Step (d) of the above method may comprise culturing the transfected cell line in media containing a GS inhibitor and selecting for transformant cells which are resistant to progressively increased level of the GS inhibitor. The media containing the GS inhibitor may further contain methionine, whereby the concentrations of GS inhibitor in the media can be reduced.

The invention is also directed to a method for using a DNA vector as a dominant selectable marker in a cotransformation process, wherein said method comprises or consists of the following steps:
 a) providing a vector according to the invention, wherein said vector comprises a sequence which encodes a recombinant protein;
 b) providing a cell line according to the invention;
 c) transfecting said cell line with said vector; and
 d) selecting transformant cells which are resistant to GS inhibitors, whereby transformant cells are selected in which a vector-derived recombinant DNA sequence which encodes GS serves as a dominant selectable and co-amplifiable marker.

In a specific embodiment of the above kits and methods, the cell line is a CHO cell line.

In a specific embodiment, the use of the combination according to the invention or of the vector according to the invention, or of the cell line according to the invention allows (i) to increase clones expressing the recombinant proteins, and/or (ii) to increase production of the recombinant protein, than when a GS of CHO origin is used.

Several documents are cited throughout the text of this specification. Each of the documents herein (including any journal article or abstract, published or unpublished patent application, issued patent, manufacturer's specifications, instructions, etc.) are hereby incorporated by reference. However, there is no admission that any document cited herein is indeed prior art in respect of the present invention.

The invention will further be described by reference to the following drawings and examples, which are illustrative only, and are not intended to limit the present invention. Indeed, the invention is defined by the claims, which should be interpreted with the help of the description and the drawings.

BRIEF DESCRIPTION OF THE SEQUENCES

SEQ ID NO: 1 shows the amino acid sequence of a GS of human origin.
SEQ ID NO: 2 shows the amino acid sequence of a GS of dog origin.
SEQ ID NO: 3 shows the amino acid sequence of a GS of Chinese hamster origin.
SEQ ID NO: 4 shows the amino acid sequence of a GS of yeast origin (*Saccharomyces cerevisiae*).
SEQ ID NO: 5 shows the amino acid sequence of a GS originating from toad (*Xenopus laevis*).
SEQ ID NO: 6 shows the amino acid sequence of a GS originating from plants (*Arabidopsis thaliana*).
SEQ ID NO: 7 shows the amino acid sequence of a GS originating from insects (*Drosophila melanogaster*).
SEQ ID NO: 8 shows a nucleotidic sequence coding for a GS of human origin.
SEQ ID NO: 9 shows a nucleotidic sequence coding for a GS of dog origin.
SEQ ID NO: 10 shows a nucleotidic sequence coding for a GS of Chinese hamster origin.
SEQ ID NO: 11 shows a nucleotidic sequence coding for a GS of yeast origin (*Saccharomyces cerevisiae*).
SEQ ID NO: 12 shows a nucleotidic sequence coding for a GS originating from toad (*Xenopus laevis*).
SEQ ID NO: 13 shows a nucleotidic sequence coding for a GS originating from plants (*Arabidopsis thaliana*).
SEQ ID NO: 14 shows a nucleotidic sequence coding for a GS originating from insects (*Drosophila melanogaster*).

EXAMPLES

Example 1

Identification of a GS Yielding Improved Results

The inventors aimed at developing new vectors for expression and production of recombinant proteins in Chinese Hamster Ovary (CHO) cell lines. A set of seven vectors was designed as described herebelow.

Two cDNAS coding for a humanized version of the 13C3 antibody (one cDNA coding for the 13C3 heavy chain and another cDNA coding for the 13C3 light chain, respectively, the combination of said chains forming the humanized 13C3 antibody) were used as reporters for assessing the quality of the vector. The murine 13C3 antibody is an antibody that specifically binds to the protofibrillar form of the human β-amyloid protein, as described in WO 2009/065054. As further used herein, the term "13C3" refers to the humanized version of the murine 13C3 antibody.

The seven vectors are schematically represented on FIG. 1. These eight vectors all comprise:
- a sequence coding for a GS, placed under the control of the early SV40 promoter;
- a first expression cassette, in which the sequence coding for the light chain of the 13C3 antibody is placed under the control of the CMV promoter;
- a second expression cassette, in which the sequence coding for the heavy chain of the 13C3 antibody is placed under the control of the CMV promoter;
- a prokaryotic origin of replication;
- a eukaryotic origin of replication; and
- a selectable marker for use in prokaryotic cells, namely a sequence coding for a protein conferring resistance to ampicillin, placed under the control of its natural promoter.

More specifically, the sequence coding for GS is placed under the control of the SV40 promoter, including the SV40 enhancer. Such an SV40 early promoter contains the SV40 72-bp tandem repeat enhancers linked to the 21-bp non tandem repeats, and the SV40 early leader protein sequence excluding any coding sequence. The use of this region as a strong promoter was described by Benoist and Chambon (1981, Nature. 290:304-10) and in Moreau et al. (1981, Nucleic Acids Res. 9:6047-68). It is classically used as a promoter for expression of selection markers in mammalian cells. In the seven pBH3694 to pBH3700 vectors, the natural HindIII restriction site that was disrupted, and unique restriction sites (SalI and XmaI) were added at the 5' and the 3' end of the promoter region, in such a way as to allow an easy swapping of the different GS cDNAs.

The seven vectors differ from one another by the sequence coding for the GS. Indeed, sequences coding for GSs having different origins were cloned into the vectors.

More specifically, seven cDNAs coding respectively for a GS from Chinese hamster (*Cricetulus griseus*), human (*Homo sapiens*), dog (*Canis lupus*), yeast (*Saccharomyces cerevisiae*), drosophila (*Drosophila melanogaster*), plant (*Arabidopsis thaliana*) and toad (*Xenopus laevis*) were generated using the naturally-occurring amino acid sequences that are available are in public databases. Starting from these sequences, the proteins were back-translated using a matrix of the most frequent codons used in CHO. Thereafter, the cDNAs were modified to contain proper cloning sites and the nucleotidic sequences were optimized. Of note, while the nucleotidic sequences were optimized for CHO expression, the amino acid sequence of encoded proteins remains identical to that of the naturally-encoded proteins.

More specifically, the naturally-occurring coding sequences for the different GS were picked in different public cDNA libraries. For instance, NCBI Reference No. NM_002065.5 was used for human GS. NCBI Reference No. NM_001002965.1 was used for dog GS. NCBI Reference No. NM_078568.2 was used for *drosophila* GS. The sequence coding for yeast GS was found in the world wide web site available at yeastgenome dot org (Reference No. YPRO35W). The Chinese hamster GS amino acid sequence corresponds to the one that is shown in NCBI Reference Sequence: XP_003502909.1 (REFSEQ: accession XM_003502861.1). Starting from the naturally-occurring cDNA sequences, the triplet codons of the sequence coding for such a GS was biased for expression in CHO cells using a software developed by Wagner and coworkers, which is based on the algorithm described in Raab et al. (2010, Syst Synth Biol. 4:215-25). This technique not only provides the best available codons for expression, but also takes into account the GC content and the absence of non desired DNA motifs.

The obtained cDNAs were cloned into the backbone bearing the expression cassettes for 13C3 antibody, thereby yielding the vectors represented on FIG. 1.

The name of these vectors as well as the origin and sequence of the encoded GS is shown in the table below.

| Name | Origin of the GS | Amino acid sequence of the GS | Nucleotidic sequence of the GS |
|---|---|---|---|
| pBH3695 | Human | SEQ ID NO: 1 | SEQ ID NO: 8 |
| pBH3700 | Dog | SEQ ID NO: 2 | SEQ ID NO: 9 |
| pBH3623 | CHO | SEQ ID NO: 3 | SEQ ID NO: 10 |
| pBH3694 | Yeast | SEQ ID NO: 4 | SEQ ID NO: 11 |
| pBH3699 | Toad | SEQ ID NO: 5 | SEQ ID NO: 12 |
| pBH3698 | Plant | SEQ ID NO: 6 | SEQ ID NO: 13 |
| pBH3697 | *Drosophila* | SEQ ID NO: 7 | SEQ ID NO: 14 |

The above vectors were nucleoporated using classical conditions into a CHO cell line. 24 hours post transfection, about 2000 cells were seeded in 480 to 960 wells of 96-well-plates, each well comprising 200 µl of CD-CHO medium containing methionine sulphoximine (msx) at a concentration of 25 µM.

About 20 days post-seeding, the media of the wells were changed to fresh and selective medium (the same as described above).

Four days later, the number of occupied was counted, i.e. the numbers of wells that are containing growing clones is counted. Each supernatant from occupied wells was tested for their 13C3 antibody productivity using an homogeneous time resolved fluorescence (HTRF) technology developed by Cisbio Bioassays (Bagnols/Ceze, France).

Figure 2:
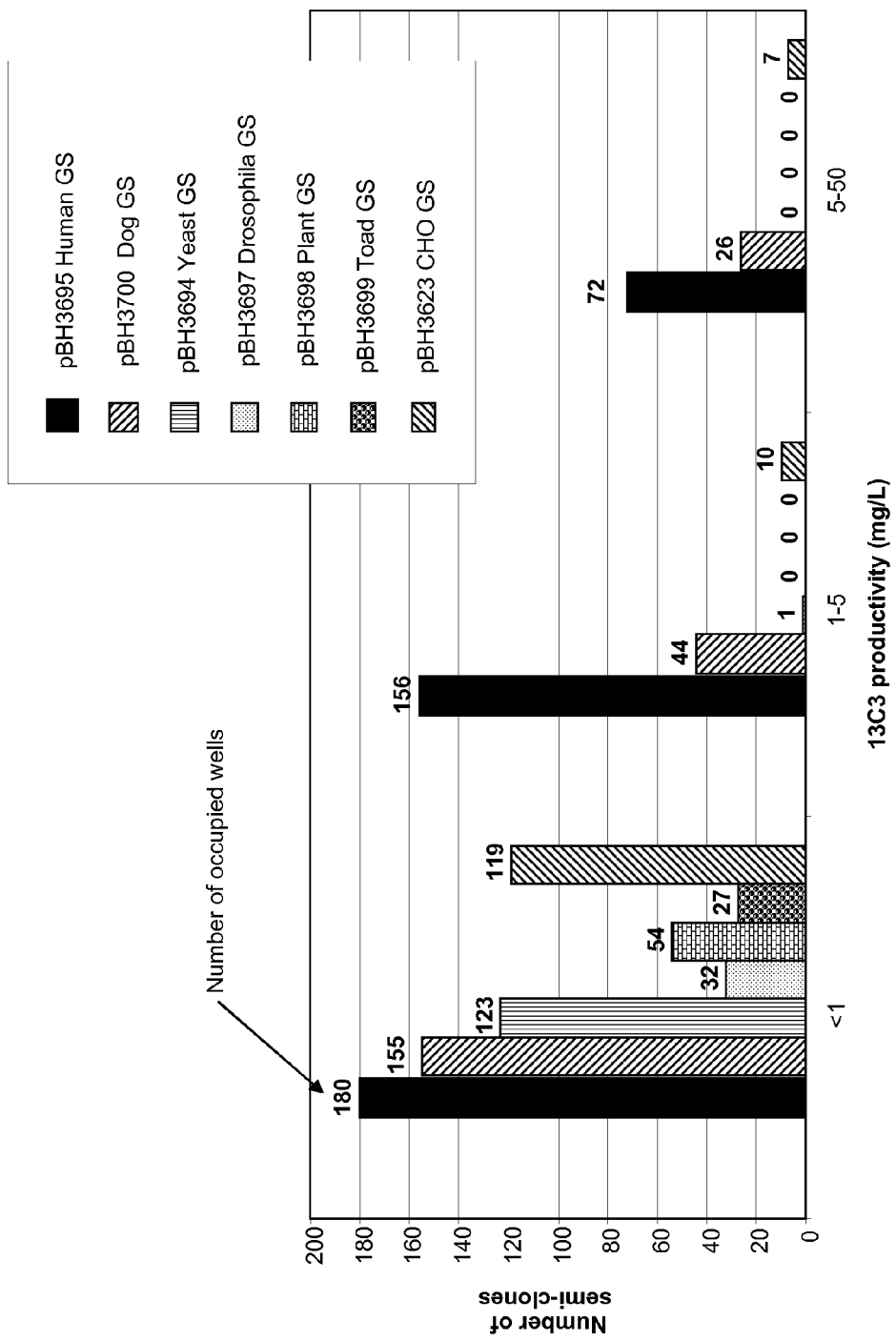
FIG. 2 shows the number of occupied wells and productivities achieved with a CHO cell line transformed with vectors pBH3695, pBH3700, pBH3694, pBH3699, pBH3698, pBH3697 and pBH3623.
Figure 3:
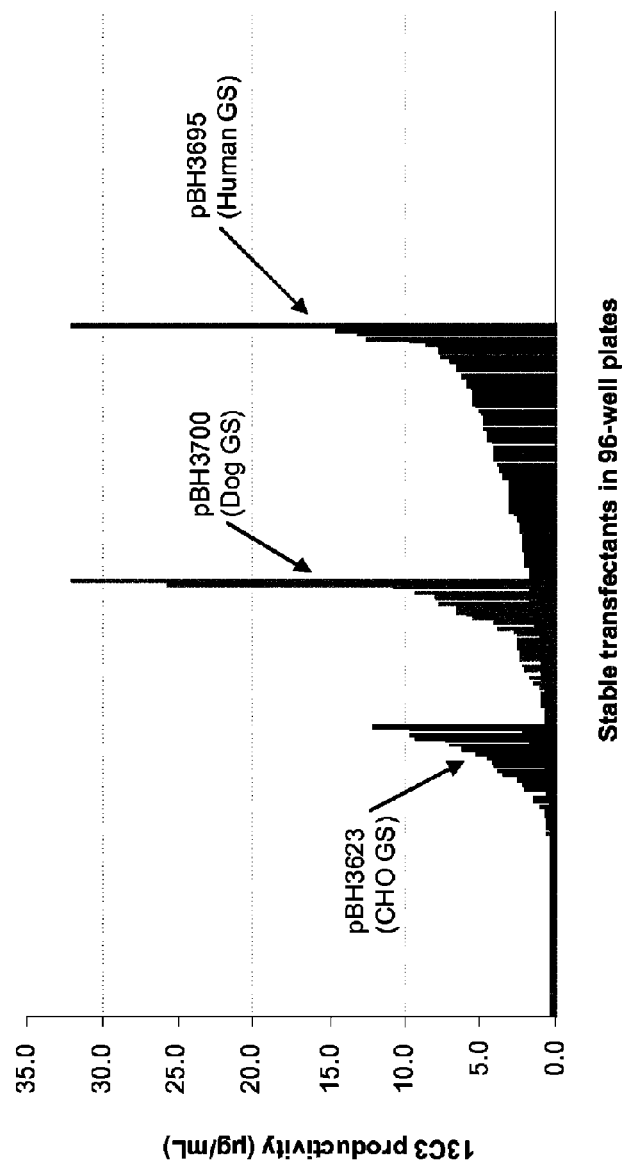
FIG. 3 shows the productivities achieved by the clones obtained during the experiment shown in FIG. 2, for vectors pBH3695, pBH3700 and pBH3623. Each bar represents a clone.

The results are shown on FIGS. 2 and 3. It can be concluded from these figures that two vectors, namely pBH3695 and PBH3700, give better results than the other vectors. They allow obtaining both more clones, and a better productivity.

Percentages of identity between sequences of different GS that were tested are shown in the three tables below. These percentages of identity were calculated using the EMBOSS Needle program, using the following default parameters:
Matrix: EBLOSUM62;
Gap_penalty: 10.0; and
Extend_penalty: 0.5.

| Vector | Sequence | Origin of GS | Percentage of identity to the human GS of SEQ ID NO: 1 |
|---|---|---|---|
| pBH3695 | SEQ ID NO: 1 | Human | 100% |
| pBH3700 | SEQ ID NO: 2 | Dog | 97.3% |
| pBH3623 | SEQ ID NO: 3 | CHO | 94.1% |
| pBH3694 | SEQ ID NO: 4 | Yeast | 52.4% |
| pBH3699 | SEQ ID NO: 5 | Toad | 85.8% |
| pBH3698 | SEQ ID NO: 6 | Plant | 50.3% |
| pBH3697 | SEQ ID NO: 7 | *Drosophila* | 62.8% |

| Vector | Sequence | Origin of GS | Percentage of identity to the dog GS of SEQ ID NO: 2 |
|---|---|---|---|
| pBH3695 | SEQ ID NO: 1 | Human | 97.3% |
| pBH3700 | SEQ ID NO: 2 | Dog | 100% |
| pBH3623 | SEQ ID NO: 3 | CHO | 94.4% |

| Vector | Sequence | Origin of GS | Percentage of identity to the CHO GS of SEQ ID NO: 3 |
|---|---|---|---|
| pBH3695 | SEQ ID NO: 1 | Human | 94.1% |
| pBH3700 | SEQ ID NO: 2 | Dog | 94.4% |
| pBH3623 | SEQ ID NO: 3 | CHO | 100% |

From these tables, it can be concluded that the two sequences that yield the best results, namely human and dog GS, are characterized in that their sequence exhibit at least 94.5% identity to the sequence of SEQ ID NO: 1 and/or 2. This feature is not true for the sequences of the other GS that were tested, which led to less optimal results.

Example 2

Confirmation of the Advantageous Properties of the Use of Vector Encoding a Human GS in a Second CHO Cell Line The above experiment has been repeated with the CHO cell line referred to as "9E4", which is suitable for industrial production of recombinant proteins.

The 9E4 cell line was established from a clone of the CHO-K1 cell line through a single cell cloning process. The CHO-K1 cell line was obtained by Puck in 1957 and has been deposited at the ATCC under number CCL-61. The CHO 9E4 cell line appears to express an endogenous and functional GS protein since this cell line can grow in the absence of glutamine. Methionine sulphoximine (msx) should thus preferably be used for selection of transfected clones.

Figure 4:
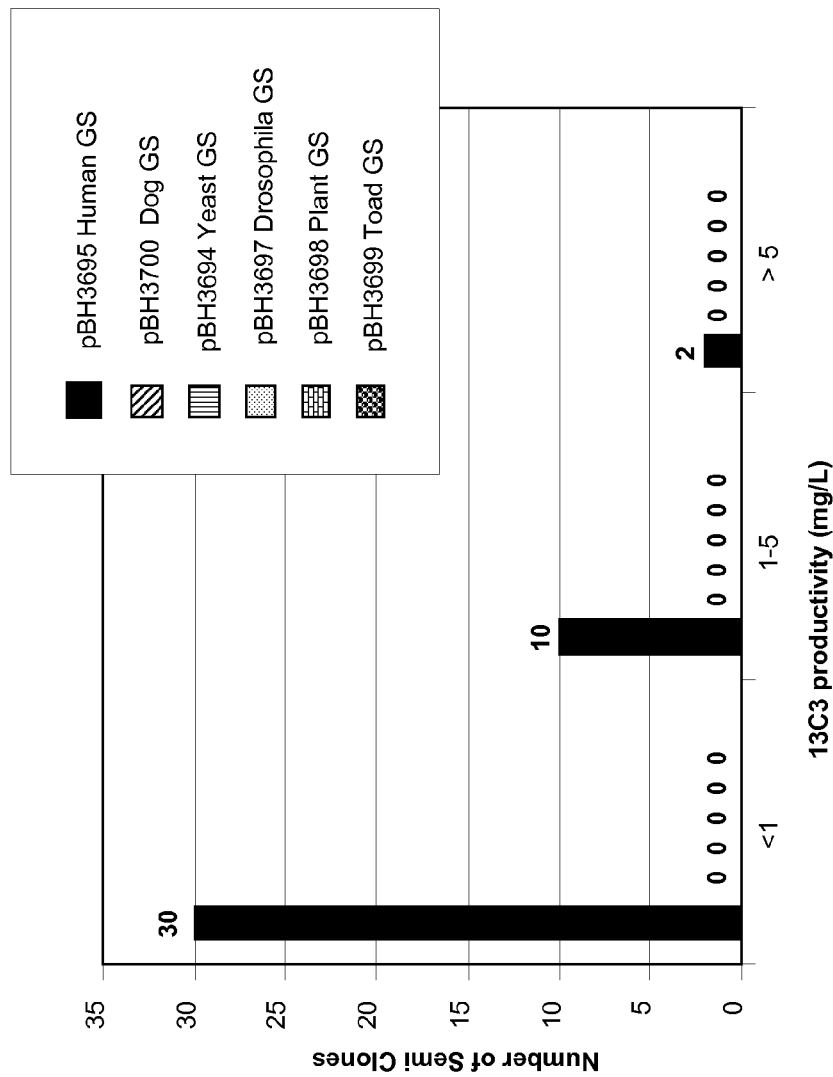
FIG. 4 shows the results of an experiment carried out in the 9E4 cell line. Productivities and the number of clones obtained are shown. The number "0" on the horizontal axis indicates that no clone was obtained (which is the case for the pBH3700, pBH3694, pBH3697, pBH3698 and pBH3699 vectors).

The vector was introduced into the 9E4 cell line through nucleoporation. A first experiment was performed using the six vectors constructed in Example 1 (namely pBH3695, pBH3700, pBH3694, pBH3697, pBH3698 and pBH3699). Conditions of selection were identical to the conditions described in Example 1 (msx added at a concentration of 25 µM). The number of occupied wells and the concentration of the 13C3 antibody were measured as described in Example 1. The results are shown on FIG. 4.

In the 9E4 cell line, pBH3695 is the only vector capable of generating clones producing 13C3 antibodies. This plasmid is the one bearing the cDNA coding for human GS, where the triplet codons were biased for expression in CHO cells. The use of a vector comprising a sequence coding for a human GS is thus particularly advantageous for producing recombinant proteins in CHO cell lines.

Example 3

Transient Expression of X14 in HEK 293 Using pBH Vector Based on Human GS and Human CMV Promoter In this experiment, a vector containing the human GS of sequence SEQ ID NO: 1 placed under the control of the SV40 promoter, and a single expression cassette containing a cDNA coding for the human or mouse X14 receptor (also named C-type lectin domain family 14, member A (CLEC14A), and respectively having the NCB! Reference Number NP_778230.1 and NP_080085.3) under the control of the human CMV promoter and a polyadenylation site, has been used. The vector containing the cDNA coding for the human X14 receptor is hereafter pBH4590 vector, and the vector containing the cDNA coding for the mouse X14 receptor is hereafter called pBH4589 vector.

The pBH4590 vector, pBH4589 vector or a control vector (i.e. an unrelated plasmid vector) were introduced by transfection with Jet PEI in HEK 293-FS cells as described by the manufacturer Poly Plus transfection.

The cells were analysed 24 h after transfection by immunofluorescence, flow cytometry or immunocytochemistry after proper labeling for human or mouse X14 detection.
Immunofluorescence Detection For immunofluorescence detection, the transfected cells were spun down and their supernatants were discarded. Cell pellets were resuspended in PBS buffer containing 1%

Bovine Serum Albumin (WN) and 0.1% Tween (V/V) (PBS T BSA) and saturated for 10 minutes in this buffer. The cells were washed twice with the same buffer and incubated with primary Serum 1 (i.e. serum obtained just before immunization of the animal, called sera pre-immune serum that represent negative control) or Serum 2 (i.e. serum that is the unpurified immune serum obtained after immunization of the animal) with purified X14 human extracellular domain as described below at dilution 1/5000 in the (PBS T BSA) buffer for 10 minutes at Room Temperature.

After washing out the unbound primary antibody, a secondary goat anti Rabbit antibody linked to an Alexa fluorophore (Alexa 488 nm Ref A11034 form Invitrogen) is added. Immunofluorescence was performed using a Leica fluorescence microscope set for detecting Alexa 488 nm.

No background Alexa 488 fluorescence can be observed either with control plasmid and serum 1 or control plasmid and serum 2, respectively. This indicates the absence of background non-specific fluorescence. On the contrary, a strong Alexa 488 fluorescence appears at the plasma membrane of cells transfected with pBH4590 and pBH4589 vectors. The use of a vector comprising a sequence coding for a human GS is thus particularly advantageous for promoting transient expression of membrane bound proteins.

flow cytometry detection.

For flow cytometry detection, human X14 labeling was achieved by two serial incubations with three different antibody preparations and a secondary antibody anti Rabbit IgG Fc moiety. The two transfected cell lines were analyzed with three different dilutions of the anti-X14 serum (1/5000, 1/1000, 1/500):

Serum 1, obtain just before immunization of the animal, called sera pre-immune serum that represent negative control, Serum 2 that is the unpurified immune serum and obtain after immunization of the animal with purified X14 human extracellular domain, Serum 3 that corresponds to the immunoglobulin fraction of Serum 2, directed against X14 human lectin.

After washing out the unbound primary antibody, a secondary goat anti Rabbit antibody linked to an Alexa fluorophore (Alexa 488 nm, Catalog Number A-11034, from Life Technologies) has been added. The transfected cells were analysed using flow cytometry set for detecting Alexa 488 with three different dilutions from Serum 1, 2 and 3 respectively.

It is worth noting that all histograms present a single fluorescence peak, indicating a homogeneous cell population. The mid fluorescence intensity of this peak is between $10^2$ and $10^3$ fluorescence units. However, cells incubated with serum 2, diluted to 1/500e, present a mid-fluorescence intensity of about 1000 fluorescence units. This minimal background intensity is suitable to study the detection at the plasma membrane. The flow cytometer was calibrated in such way that the fluorescence observed with control vector and serum 1 diluted to 1/5000e, was taken as background reference fluorescence.

Cells transfected with pBH4590 vector were then analyzed. Fluorescence intensity of human X14 transfected cell with serum 1, for each dilution, is similar to the signals of the control cells. On the contrary, the fluorescence signals were markedly more intense for serum 2 and purified polyclonal antibodies (Serum 3) than for pre-immune serum (Serum 1). In fact, mid fluorescence intensity for immune serum (Serum 2) and purified antibody (Serum 3) on human X14 transfected cells is $10^4$ fluorescence units. It increases by a factor of 10-20 at the three concentrations of specific antisera tested.

These results demonstrate that in HEK 293-FS cells transfected with pBH4590 vector, human X14 is produced at a clearly detectable level as observed by fluorescent microscopy and flow cytometry. Moreover human X14 is being accessible to extracellular detection indicating that it is expressed at the plasma membrane.

Example 4

Expression of Human and Murine X14 Receptors in CHO Cells

The goal of this experiment was to test if the same vector that was used for transient human or mouse X14 expression could be used for expression in CHO cells as stable clones of either mouse or human X14 receptor. To do so the pBH4590 vector or pBH4589 vector bearing human GS cDNA was transfected into CHO-9E4 cell line, using the protocol developed by Lonza/Amaxa nucleoporation device. Two millions CHO-9E4 cells were electroporated with 10 µg of the pBH4590 vector or pBH4589 vector described hereabove. Soon After the electric shock, the cells were diluted into 2 ml CD-CHO fresh medium and 24 hours later, the cells were again diluted into fresh CD-CHO medium containing 25 µM methyl sulfoximide (msx) at a concentration of 10 000 cells per ml. About ten 96 well plates were seeded at 2000 cells per well. CHO semi clones, obtained after CHO cells transfection with pBH4590 vector or pBH4589 vector, using the selectable marker GS, were screened. A transfection with the reference control expressing antibody 13C3 was also performed. Said control was used as control for analysis by flow cytometer. Thirty human X14 semi clones, forty-one mouse X14 semi clones and twenty-nine semi clones for control vector were obtained.

After the passage of semi clones in 24-well plates, that is at the beginning of the amplification process, the detection of presence or absence of human or mouse X14 antigen using tools described previously has been performed.

It has been observed that, for example, the human semi clone n° 12 has fluorescence intensity lower than the murine semi clone n° 30. In fact, with murine semi clones, the presence of single peak fluorescence having a maximum fluorescence intensity of $10^3$ fluorescence units was observed, while in the case of human semi clone, peak is spread and the mean fluorescence intensity does not exceed 500 fluorescence units. Amplification of semi clones which were analyzed as positive by flow cytometry was performed, thereby allowing to finally generate 10 semi clones of CHO lines stably expressing X14 murine lectin and 4 semi clones of CHO lines stably expressing X14 human lectin.

The use of a vector comprising a sequence coding for a human GS is thus particularly advantageous for generating CHO lines stably expressing recombinant proteins.

Example 5

Transient Transfection in CHO-S of Different DNA Plasmid Coding for Different Two Different Antibodies In order to study the feasibility of using our vector bearing the human GS cDNAs for transient transfection in CHO-S, a second vector, called, derived from the pBH3695 was constructed by replacing the two cDNAs corresponding to the light and heavy chain of the 13C3 antibody by the light and heavy chain of the anti-CD38 cDNAs using classical cloning technologies and four different unique restriction sites. Consequently, the pBH3772 vector comprises:
- a sequence coding for a GS, placed under the control of the early SV40 promoter;
- a first expression cassette, in which the sequence coding for the light chain of the anti-CD38 antibody is placed under the control of the CMV promoter;
- a second expression cassette, in which the sequence coding for the heavy chain of the anti-CD38 antibody is placed under the control of the CMV promoter;
- a prokaryotic origin of replication;
- an eukaryotic origin of replication; and
- a selectable marker for use in prokaryotic cells, namely a sequence coding for a protein conferring resistance to ampicillin, placed under the control of its natural promoter.

CHO-S were then transfected using the Maxcyte® apparatus with (i) two control vectors classically used for transient transfection and containing the cDNA of light and heavy chain of two different antibodies (i.e. called Control 1 and Control 2), and (ii) the pBH3695 and pBH3772 vectors in the conditions described by Maxcyte® Corporation. CHO-S cells were cultivated in CD-CHO containing 8 mM Glutamine in classical CHO-S cultivating conditions (Passage every 2-3 days at 0.3 $10^6$ cells/ml). The day before transfection, the cells were splitted to 1.2 $10^6$ cells/ml and transfected 24 hours later. Temperature shift and media feeding were done according to the Maxcyte® protocol. Culture samples were taken at day 3, 6, 7, 8 and 9, and measured by SEC-HPLC using purified antibody as standard reference curve.

Figure 6:
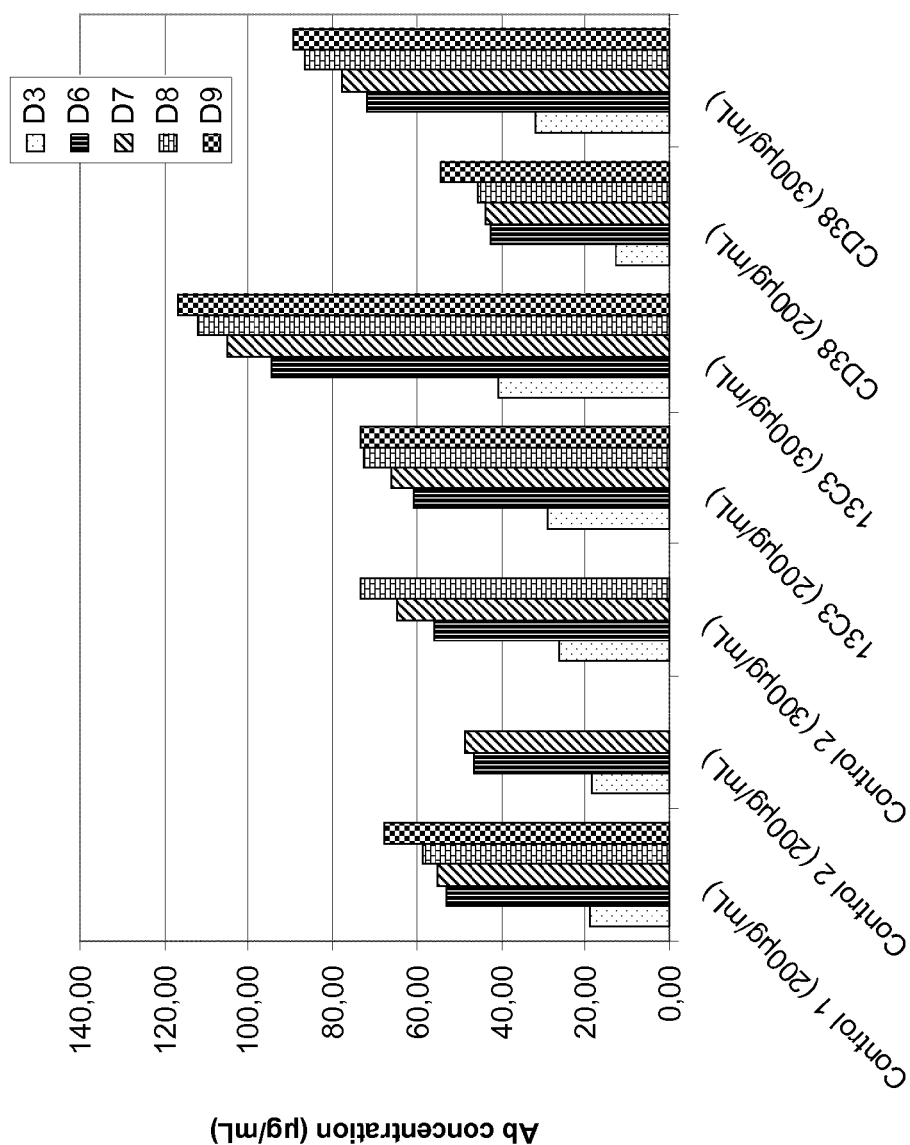
FIG. 6 shows the antibody concentration obtained after transient transfection of CHO-S cells with control vectors (Control 1 and Control 2), and with the pBH3695 and pBH3772 vectors, respectively expressing the 13C3 and anti-CD38 antibodies.

Results of such an experiment are shown on the FIG. 6.

It can be concluded from this figure that the pBH3695 and pBH3772 vectors are capable of producing antibodies at level that are equivalent or better than the two control vectors classically used for transient transfection.

In conclusion the two pBH3695 and pBH3772 vectors based on human Glutamine Synthase are capable of producing remarkable level of antibodies above 100 mg/l.

The use of a vector comprising a sequence coding for a human GS is thus particularly advantageous for stably or transiently expressing membrane bound protein or antibodies.

Example 6

Expression of Human Erythropoietin (EPO) in CHO Cells

In order to perform the expression of human EPO, the pBH4590 vector was digested with restriction enzymes NheI and EcoRI and two human EPO cDNA, i.e. cDNA1 or cDNA2 bordered with NheI and EcoRI sites, were inserted in said vector using classical molecular biology techniques.

This allows to obtain the pBH4614 vector bearing the human EPO cDNA1, and the pBH4615 vector bearing the human EPO cDNA2.

The two vectors were prepared at the maxi-preparation level using a kit developed by Qiagen corporation.

pBH4614 and pBH4615 vectors were used to transfect the three cell lines CHO-S, CHO-9E4 and CHO 30D12 using the Lonza electroporation techniques, respectively. To do so, the cells were splitted the day before transfection to achieve a cellular density of 1×$10^6$ cells/ml. Two millions cells were spun down and suspended in 100 µl solution V in the presence of 10 µg of DNA, respectively for each DNA and cell line. Cells were electroporated using program X05. Rapidly after electroporation, the cells were diluted into 2 ml of CD-CHO medium containing 6 mM glutamine (Life Technologies) and incubated for 24 hours at 37° C. and 5% CO2. After this incubation, the cells are diluted into 200 ml of the same medium without Glutamine and in the presence of 25 µM msx and distributed in 96 well plates using 200 µl per well. After 15 (CHO-S) to 25 days (CHO-9E4, CHO 30D12), fresh medium was changed in wells containing surviving cells. Four to 5 days later, the surviving cells were transferred into 1 ml of CD-CHO containing 25 µM msx without agitation respectively for each well. For CHO-S, 24 semi-clones were amplified, meanwhile 12 semi clones were amplified for the two other cell lines, respectively for the two EPO cDNA. Overall 96 semi-clones were amplified, grown and verified for their capacity to produce human erythropoietin. To do so, after 3-4 day incubation, the 1 ml were diluted into 4 ml of the CD-CHO medium containing 25 µM msx and put into agitation at 37° C. and 5% CO2. After 3-4 days, the cultures were again diluted with 5 ml fresh medium. After 3-4 days, the cellular density was measured and cells were diluted at 3×$10^5$ cells/ml and grown for 3-4 days for a first time. Cellular density was measured and cells were seeded at 3×$10^5$ cells/ml in CD-CHO medium containing 25 µM msx and 30% Feed B (Life Technologies).

Cells were grown in 10 ml of the above medium (37° C. 5% $CO_2$) for 10 days. Cellular density and viability were measured after 8 and 10 days. 0.6 ml samples were equally taken to evaluate human EPO concentration. Culture supernatants (0.6 ml) were first screened using the microfluidic Caliper technology evaluating the presence of protein at the apparent molecular weight of human EPO.

Sixteen best clone supernatants, e.g. having the most intense EPO signal, were submitted to an ELISA specific for human EPO detection using the kit developed by R&D System® for in vitro diagnostic (Human Erythropoietin Quantikine® IVD ELISA Kit For In Vitro Diagnostic Use, Catalog reference DEP00). Seven clones were shown to have interesting productivities as measured at Day 8 and Day 10 (Table below).

| Semi clones | Viable cells/ml (×10^6) Day 8 | Viable cells/ml (×10^6) Day 10 | EPO Concentration (g/L) Day 8 | EPO Concentration (g/L) Day 10 |
|---|---|---|---|---|
| CHO-S cDNA1/clone 17 | 3.9 | 0.4 | 0.9 | 1.5 |
| CHO-S cDNA1/clone 18 | 9.8 | 5.8 | 0.5 | 1.0 |
| CHO-S cDNA1/clone 21 | 2.4 | 2.6 | 0.5 | 0.9 |
| CHO-S cDNA1/clone 24 | 1.4 | 1.5 | 0.5 | 0.9 |
| CHO-S cDNA2/clone 30 | 4.6 | 1.5 | 0.4 | 0.6 |
| CHO-30D12 cDNA2/clone 90 | 8.4 | 0.8 | 1.1 | 2.0 |
| CHO-30D12 cDNA2/clone 92 | 19.4 | 20.3 | 0.4 | 0.7 |
| CHO-30D12 cDNA2/clone 93 | 23.1 | 26.7 | 0.3 | 0.7 |
| CHO-30D12 cDNA2/clone 94 | 18.8 | 17.8 | 1.3 | 1.4 |

The productivities of the clones were ranging from 0.3 to 2.0 g/l. Semi-clone 90 was the best producing clone with a productivity of 1.1 to 2.0 g/L at Day 8 and Day 10 respectively.

The viability of this clone at Day 10 was around 70% with less than one million cells per ml (0.8 million cells/ml) rendering impossible to calculate the specific productivity as the number of cells is diminishing between Day 8 and Day 10. It renders not possible the calculation of a specific activity (Table below). This phenomenon is observed for most the semi-clones except for semi-clones 21, 24, 92 and 93. In that case, the specific productivity expressed in µg/106 cells/day can go up to 441 and 854 (Table below).

| Semi clones | Daily Growth Rate | Productivity pg/cell in 2 days | Specific Productivity (pg/cell/day) |
|---|---|---|---|
| CHO-S cDNA1/clone 17 | NA | NA | NA |
| CHO-S cDNA1/clone 18 | NA | NA | NA |
| CHO-S cDNA1/clone 21 | 0.29 | 1542 | 441 |
| CHO-S cDNA1/clone 24 | 0.17 | 5125 | 854 |
| CHO-S cDNA2/clone 30 | NA | NA | NA |
| CHO-30D12 cDNA2/clone 90 | NA | NA | NA |
| CHO-30D12 cDNA2/clone 92 | 0.12 | 296 | 36 |
| CHO-30D12 cDNA2/clone 93 | 0.43 | 117 | 51 |
| CHO-30D12 cDNA2/clone 94 | NA | 117 | NA |

These results thus shown that, both in terms of volume or specific productivity, the use of a vector comprising a sequence coding for a human GS allow having productivity above than 300 µg of protein per million cells.

The invention claimed is:

1. A Chinese Hamster Ovary (CHO) cell line comprising a deoxyribonucleic acid (DNA) expression vector, and wherein said vector comprises: a nucleotide sequence coding for a mammalian glutamine synthetase (GS) comprising a sequence at least 80% identical to the sequence of SEQ ID NO: 8 or SEQ ID NO: 9 operably linked to a heterologous promoter; and at least one expression cassette for expressing a recombinant protein, wherein said GS comprises a protein sequence at least 94.5% identical to the sequence of SEQ ID NO: 1 or to the sequence of SEQ ID NO: 2.

2. The CHO cell line according to claim 1, wherein said GS is a human GS.

3. The CHO cell line according to claim 1, wherein said GS comprises the sequence of SEQ ID NO: 1.

4. The CHO cell line according to claim 1, wherein said sequence coding for a GS comprises the sequence of SEQ ID NO: 8 or SEQ ID NO: 9.

5. The CHO cell line according to claim 1, wherein said sequence coding for mammalian GS is placed under the control of a Simian vacuolating virus 40 (SV40) promoter.

6. The CHO cell line according to claim 1, wherein said recombinant protein is a monoclonal antibody.

7. The CHO cell line according to claim 6, wherein said vector comprises a first expression cassette suitable for cloning of an antibody light chain, and
a second expression cassette suitable for cloning of an antibody heavy chain.

8. The CHO cell line according to claim 7, wherein said first and second expression cassettes each comprise a CMV promoter.

9. The CHO cell line according to claim 1, wherein the cell line allows obtaining clones producing at least 1 mg/L of recombinant protein.

10. A deoxyribonucleic acid (DNA) expression vector, wherein said vector comprises: a nucleotide sequence coding for a mammalian glutamine synthetase (GS) comprising a sequence at least 80% identical to the sequence of SEQ ID NO: 8 or SEQ ID NO: 9 under the control of a Simian vacuolating virus 40 (SV40) promoter, a first expression cassette for cloning of a heterologous recombinant protein under the control of a CMV promoter, wherein said GS comprises a protein sequence at least 94.5% identical to the sequence of SEQ ID NO: 1 or to the sequence of SEQ ID NO: 2.

11. The DNA vector according to claim 10, wherein said heterologous recombinant protein is a monoclonal antibody.

12. A deoxyribonucleic acid (DNA) expression vector, wherein said vector comprises: a nucleotide sequence coding for a mammalian glutamine synthetase (GS) comprising a sequence at least 80% identical to the sequence of SEQ ID NO: 8 or SEQ ID NO: 9 under the control of a Simian vacuolating virus 40 (SV40) promoter, a first expression cassette for cloning of an antibody light chain under the control of a CMV promoter, and a second expression cassette suitable for cloning of an antibody heavy chain under the control of a CMV promoter, wherein said GS comprises a protein sequence at least 94.5% identical to the sequence of SEQ ID NO: 1 or to the sequence of SEQ ID NO: 2.

13. A combination of:
(i) a Chinese Hamster Ovary (CHO) cell line; and
(ii) a DNA (deoxyribonucleic acid) vector for production of a recombinant protein, wherein said vector comprises a sequence coding for a mammalian glutamine synthetase (GS) comprising a sequence at least 80% identical to the sequence of SEQ ID NO: 8 or SEQ ID NO: 9 operably linked to a heterologous promoter, wherein said GS comprises a protein sequence at least 94.5% identical to the sequence of SEQ ID NO: 1 or to the sequence of SEQ ID NO: 2.

14. A kit comprising the combination according to claim 13.

15. An in vitro method of producing a recombinant protein comprising the steps of:
a) providing a CHO cell line according to claim 1;
b) culturing said CHO cell line obtained under conditions for production of the recombinant protein; and
c) isolating and/or purifying said recombinant protein.

16. The method according to claim 15, further comprising the step of formulating said recombinant protein into a pharmaceutical composition.

* * * * *

SEQUENCE LISTING

<160> NUMBER OF SEQ ID NOS: 14

<210> SEQ ID NO 1
<211> LENGTH: 373
<212> TYPE: PRT
<213> ORGANISM: Homo sapiens

<400> SEQUENCE: 1

```
Met Thr Thr Ser Ala Ser Ser His Leu Asn Lys Gly Ile Lys Gln Val
1               5                   10                  15

Tyr Met Ser Leu Pro Gln Gly Glu Lys Val Gln Ala Met Tyr Ile Trp
            20                  25                  30

Ile Asp Gly Thr Gly Glu Gly Leu Arg Cys Lys Thr Arg Thr Leu Asp
        35                  40                  45

Ser Glu Pro Lys Cys Val Glu Glu Leu Pro Glu Trp Asn Phe Asp Gly
    50                  55                  60

Ser Ser Thr Leu Gln Ser Glu Gly Ser Asn Ser Asp Met Tyr Leu Val
65                  70                  75                  80

Pro Ala Ala Met Phe Arg Asp Pro Phe Arg Lys Asp Pro Asn Lys Leu
                85                  90                  95

Val Leu Cys Glu Val Phe Lys Tyr Asn Arg Arg Pro Ala Glu Thr Asn
            100                 105                 110

Leu Arg His Thr Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Arg Ala Tyr Gly Arg Asp Ile Val
                165                 170                 175

Glu Ala His Tyr Arg Ala Cys Leu Tyr Ala Gly Val Lys Ile Ala Gly
            180                 185                 190

Thr Asn Ala Glu Val Met Pro Ala Gln Trp Glu Phe Gln Ile Gly Pro
        195                 200                 205

Cys Glu Gly Ile Ser Met Gly Asp His Leu Trp Val Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Tyr Ile Glu Glu
```

```
                    260                 265                 270
Ala Ile Glu Lys Leu Ser Lys Arg His Gln Tyr His Ile Arg Ala Tyr
                275                 280                 285

Asp Pro Lys Gly Gly Leu Asp Asn Ala Arg Arg Leu Thr Gly Phe His
            290                 295                 300

Glu Thr Ser Asn Ile Asn Asp Phe Ser Ala Gly Val Ala Asn Arg Ser
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ser Val Thr
            340                 345                 350

Glu Ala Leu Ile Arg Thr Cys Leu Leu Asn Glu Thr Gly Asp Glu Pro
        355                 360                 365

Phe Gln Tyr Lys Asn
        370

<210> SEQ ID NO 2
<211> LENGTH: 373
<212> TYPE: PRT
<213> ORGANISM: Canis lupus

<400> SEQUENCE: 2

Met Ala Thr Ser Ala Ser Ser His Leu Asn Lys Gly Ile Lys Gln Val
1               5                   10                  15

Tyr Met Ser Leu Pro Gln Gly Glu Lys Val Gln Ala Met Tyr Ile Trp
            20                  25                  30

Ile Asp Gly Thr Gly Glu Gly Leu Arg Cys Lys Thr Arg Thr Leu Asp
        35                  40                  45

Ser Glu Pro Lys Gly Val Glu Glu Leu Pro Glu Trp Asn Phe Asp Gly
    50                  55                  60

Ser Ser Thr Phe Gln Ser Glu Gly Ser Asn Ser Asp Met Tyr Leu Val
65                  70                  75                  80

Pro Ala Ala Met Phe Arg Asp Pro Phe Arg Lys Asp Pro Asn Lys Leu
                85                  90                  95

Val Phe Cys Glu Val Phe Lys Tyr Asn Arg Lys Pro Ala Glu Thr Asn
            100                 105                 110

Leu Arg His Thr Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Ile Lys Ile Ala Gly
            180                 185                 190

Thr Asn Ala Glu Val Met Pro Ala Gln Trp Glu Phe Gln Ile Gly Pro
        195                 200                 205

Cys Glu Gly Ile Asp Met Gly Asp His Leu Trp Val Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255
```

```
Ser Thr Lys Ala Met Arg Glu Glu Asn Gly Leu Lys Tyr Ile Glu Glu
            260                 265                 270

Ser Ile Glu Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Gly
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ser Val Thr
            340                 345                 350

Glu Ala Leu Ile Arg Thr Cys Leu Leu Asn Glu Thr Gly Asp Glu Pro
        355                 360                 365

Phe Gln Tyr Lys Asn
        370

<210> SEQ ID NO 3
<211> LENGTH: 373
<212> TYPE: PRT
<213> ORGANISM: Cricetulus griseus

<400> SEQUENCE: 3

Met Ala Thr Ser Ala Ser Ser His Leu Asn Lys Asn Ile Lys Gln Met
1               5                   10                  15

Tyr Leu Cys Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Glu Leu Pro Glu Trp Asn Phe Asp Gly
50                  55                  60

Ser Ser Thr Phe Gln Ser Glu Gly Ser Asn Ser Asp Met Tyr Leu Ser
65                  70                  75                  80

Pro Val Ala Met Phe Arg Asp Pro Phe Arg Arg Asp Pro Asn Lys Leu
                85                  90                  95

Val Phe Cys Glu Val Phe Lys Tyr Asn Arg Lys Pro Ala Glu Thr Asn
            100                 105                 110

Leu Arg His Ser Cys Lys Arg Ile Met Asp Met Val Ser Asn Gln His
        115                 120                 125

Pro Trp Phe Gly Met Glu Gln Glu Tyr Thr Leu Met Gly Thr Asp Gly
130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Val Ala Arg Phe Ile
210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255
```

```
Ser Thr Lys Ala Met Arg Glu Glu Asn Gly Leu Lys His Ile Glu Glu
            260                 265                 270

Ala Ile Glu Lys Leu Ser Lys Arg His Arg Tyr His Ile Arg Ala Tyr
            275                 280                 285

Asp Pro Lys Gly Gly Leu Asp Asn Ala Arg Arg Leu Thr Gly Phe His
            290                 295                 300

Glu Thr Ser Asn Ile Asn Asp Phe Ser Ala Gly Val Ala Asn Arg Ser
305                 310                 315                 320

Ala Ser Ile Arg Ile Pro Arg Thr Val Gly Gln Lys Lys Gly Tyr
                325                 330                 335

Phe Glu Asp Arg Arg Pro Ser Ala Asn Cys Asp Pro Phe Ala Val Thr
            340                 345                 350

Glu Ala Ile Val Arg Thr Cys Leu Leu Asn Glu Thr Gly Asp Glu Pro
            355                 360                 365

Phe Gln Tyr Lys Asn
    370

<210> SEQ ID NO 4
<211> LENGTH: 370
<212> TYPE: PRT
<213> ORGANISM: Saccharomyces cerevisiae

<400> SEQUENCE: 4

Met Ala Glu Ala Ser Ile Glu Lys Thr Gln Ile Leu Gln Lys Tyr Leu
1               5                   10                  15

Glu Leu Asp Gln Arg Gly Arg Ile Ile Ala Glu Tyr Val Trp Ile Asp
            20                  25                  30

Gly Thr Gly Asn Leu Arg Ser Lys Gly Arg Thr Leu Lys Lys Arg Ile
            35                  40                  45

Thr Ser Ile Asp Gln Leu Pro Glu Trp Asn Phe Asp Gly Ser Ser Thr
50                  55                  60

Asn Gln Ala Pro Gly His Asp Ser Asp Ile Tyr Leu Lys Pro Val Ala
65                  70                  75                  80

Tyr Tyr Pro Asp Pro Phe Arg Arg Gly Asp Asn Ile Val Val Leu Ala
            85                  90                  95

Ala Cys Tyr Asn Asn Asp Gly Thr Pro Asn Lys Phe Asn His Arg His
            100                 105                 110

Glu Ala Ala Lys Leu Phe Ala Ala His Lys Asp Glu Glu Ile Trp Phe
            115                 120                 125

Gly Leu Glu Gln Glu Tyr Thr Leu Phe Asp Met Tyr Asp Asp Val Tyr
            130                 135                 140

Gly Trp Pro Lys Gly Gly Tyr Pro Ala Pro Gln Gly Pro Tyr Tyr Cys
145                 150                 155                 160

Gly Val Gly Ala Gly Lys Val Tyr Ala Arg Asp Met Ile Glu Ala His
            165                 170                 175

Tyr Arg Ala Cys Leu Tyr Ala Gly Leu Glu Ile Ser Gly Ile Asn Ala
            180                 185                 190

Glu Val Met Pro Ser Gln Trp Glu Phe Gln Val Gly Pro Cys Thr Gly
            195                 200                 205

Ile Asp Met Gly Asp Gln Leu Trp Met Ala Arg Tyr Phe Leu His Arg
            210                 215                 220

Val Ala Glu Glu Phe Gly Ile Lys Ile Ser Phe His Pro Lys Pro Leu
225                 230                 235                 240

Lys Gly Asp Trp Asn Gly Ala Gly Cys His Ala Asn Val Ser Thr Lys
```

245                 250                 255
Glu Met Arg Gln Pro Gly Gly Thr Lys Tyr Ile Glu Gln Ala Ile Glu
            260                 265                 270

Lys Leu Ser Lys Arg His Ala Glu His Ile Lys Leu Tyr Gly Ser Asp
            275                 280                 285

Asn Asp Met Arg Leu Thr Gly Arg His Glu Thr Ala Ser Met Thr Ala
            290                 295                 300

Phe Ser Ser Gly Val Ala Asn Arg Gly Ser Ser Ile Arg Ile Pro Arg
305                 310                 315                 320

Ser Val Ala Lys Glu Gly Tyr Gly Tyr Phe Glu Asp Arg Arg Pro Ala
                325                 330                 335

Ser Asn Ile Asp Pro Tyr Leu Val Thr Gly Ile Met Cys Glu Thr Val
                340                 345                 350

Cys Gly Ala Ile Asp Asn Ala Asp Met Thr Lys Glu Phe Glu Arg Glu
                355                 360                 365

Ser Ser
    370

<210> SEQ ID NO 5
<211> LENGTH: 373
<212> TYPE: PRT
<213> ORGANISM: Xenopus laevis

<400> SEQUENCE: 5

Met Ala Thr Ser Ala Ser Ala Gln Leu Ser Lys Ala Ile Lys Gln Met
1               5                   10                  15

Tyr Leu Glu Leu Pro Gln Gly Asp Lys Val Gln Ala Met Tyr Ile Trp
            20                  25                  30

Ile Asp Gly Thr Gly Glu Gly Leu Arg Cys Lys Thr Arg Thr Leu Asp
            35                  40                  45

Ser Glu Pro Lys Thr Ile Glu Asp Leu Pro Glu Trp Asn Phe Asp Gly
    50                  55                  60

Ser Ser Thr His Gln Ser Glu Gly Ser Asn Ser Asp Met Tyr Leu Ile
65                  70                  75                  80

Pro Val Ala Met Phe Arg Asp Pro Phe Arg Arg Asp Pro Asn Lys Leu
                85                  90                  95

Val Leu Cys Glu Val Leu Lys Tyr Asn Arg Lys Thr Ala Glu Thr Asn
            100                 105                 110

Leu Arg His Thr Cys Asn Gln Ile Met Asp Met Val Gly Asn Glu His
            115                 120                 125

Pro Trp Phe Gly Met Glu Gln Glu Tyr Thr Leu Leu Gly Met Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asn Lys Ala Tyr Gly Arg Asp Ile Val
                165                 170                 175

Glu Ala His Tyr Arg Ala Cys Leu Tyr Ala Gly Val Lys Ile Ala Gly
            180                 185                 190

Thr Asn Ala Glu Val Met Pro Ala Gln Trp Glu Phe Gln Ile Gly Thr
            195                 200                 205

Cys Glu Gly Ile Asp Met Gly Asp His Leu Trp Ile Ala Arg Phe Ile
    210                 215                 220

Leu His Arg Val Cys Glu Asp Phe Gly Ile Ile Val Ser Phe Asp Pro
225                 230                 235                 240

```
Lys Pro Ile Thr Gly Asn Trp Asn Gly Ala Gly Cys His Thr Asn Phe
                245                 250                 255

Ser Thr Lys Ser Met Arg Glu Glu Gly Leu Lys His Ile Glu Glu
        260                 265                 270

Ser Ile Glu Arg Leu Ser Lys Arg His Glu Tyr His Ile Arg Met Tyr
        275                 280                 285

Asp Pro Arg Gly Gly Lys Asp Asn Ala Arg Arg Leu Thr Gly Phe His
    290                 295                 300

Glu Thr Ser Ser Ile His Glu Phe Ser Ala Gly Val Ala Asn Arg Gly
305                 310                 315                 320

Ala Ser Ile Arg Ile Pro Arg Leu Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Val Ile Arg Thr Cys Leu Leu Asn Glu Thr Gly Asp Glu Pro
        355                 360                 365

Leu Glu Tyr Lys Asn
    370

<210> SEQ ID NO 6
<211> LENGTH: 354
<212> TYPE: PRT
<213> ORGANISM: Arabidopsis thaliana

<400> SEQUENCE: 6

Met Ser Leu Leu Ser Asp Leu Val Asn Leu Asn Leu Thr Asp Ala Thr
1               5                   10                  15

Gly Lys Ile Ile Ala Glu Tyr Ile Trp Ile Gly Gly Ser Gly Met Asp
                20                  25                  30

Ile Arg Ser Lys Ala Arg Thr Leu Pro Gly Pro Val Thr Asp Pro Ser
            35                  40                  45

Lys Leu Pro Lys Trp Asn Tyr Asp Gly Ser Ser Thr Gly Gln Ala Ala
        50                  55                  60

Gly Glu Asp Ser Glu Val Ile Leu Tyr Pro Gln Ala Ile Phe Lys Asp
65                  70                  75                  80

Pro Phe Arg Lys Gly Asn Asn Ile Leu Val Met Cys Asp Ala Tyr Thr
                85                  90                  95

Pro Ala Gly Asp Pro Ile Pro Thr Asn Lys Arg His Asn Ala Ala Lys
            100                 105                 110

Ile Phe Ser His Pro Asp Val Ala Lys Glu Glu Pro Trp Tyr Gly Ile
        115                 120                 125

Glu Gln Glu Tyr Thr Leu Met Gln Lys Asp Val Asn Trp Pro Ile Gly
    130                 135                 140

Trp Pro Val Gly Gly Tyr Pro Gly Pro Gln Gly Pro Tyr Tyr Cys Gly
145                 150                 155                 160

Val Gly Ala Asp Lys Ala Ile Gly Arg Asp Ile Val Asp Ala His Tyr
                165                 170                 175

Lys Ala Cys Leu Tyr Ala Gly Ile Gly Ile Ser Gly Ile Asn Gly Glu
            180                 185                 190

Val Met Pro Gly Gln Trp Glu Phe Gln Val Gly Pro Val Glu Gly Ile
        195                 200                 205

Ser Ser Gly Asp Gln Val Trp Val Ala Arg Tyr Leu Leu Glu Arg Ile
    210                 215                 220

Thr Glu Ile Ser Gly Val Ile Val Ser Phe Asp Pro Lys Pro Val Pro
225                 230                 235                 240
```

Gly Asp Trp Asn Gly Ala Gly Ala His Cys Asn Tyr Ser Thr Lys Thr
                245                 250                 255

Met Arg Asn Asp Gly Gly Leu Glu Val Ile Lys Lys Ala Ile Gly Lys
            260                 265                 270

Leu Gln Leu Lys His Lys Glu His Ile Ala Ala Tyr Gly Glu Gly Asn
        275                 280                 285

Glu Arg Arg Leu Thr Gly Lys His Glu Thr Ala Asp Ile Asn Thr Phe
    290                 295                 300

Ser Trp Gly Val Ala Asn Arg Gly Ala Ser Val Arg Val Gly Arg Asp
305                 310                 315                 320

Thr Glu Lys Glu Gly Lys Gly Tyr Phe Glu Arg Arg Pro Ala Ser
                325                 330                 335

Asn Met Asp Pro Tyr Val Val Thr Ser Met Ile Ala Glu Thr Thr Ile
            340                 345                 350

Leu Gly

<210> SEQ ID NO 7
<211> LENGTH: 369
<212> TYPE: PRT
<213> ORGANISM: Drosophila melanogaster

<400> SEQUENCE: 7

Met Ser Ala Arg Ile Leu Glu Asp Ser Pro Asn Ala Arg Ile Asn Lys
1               5                   10                  15

Thr Ile Leu Asp Arg Tyr Leu Ser Leu Pro Leu Gln Glu Asn Ile Val
            20                  25                  30

Gln Ala Thr Tyr Val Trp Ile Asp Gly Thr Gly Glu Asp Leu Arg Cys
        35                  40                  45

Lys Asp Arg Thr Leu Asp Phe Ile Pro Gln Ser Pro Lys Glu Leu Pro
    50                  55                  60

Val Trp Asn Tyr Asp Gly Ser Ser Cys Tyr Gln Ala Glu Gly Ser Asn
65                  70                  75                  80

Ser Asp Thr Tyr Leu Tyr Pro Val Ala Ile Tyr Lys Asp Pro Phe Arg
                85                  90                  95

Arg Gly Asn Asn Ile Leu Val Met Cys Asp Thr Tyr Lys Phe Asp Gly
            100                 105                 110

Thr Pro Thr Asp Thr Asn Lys Arg Lys Thr Cys Leu Glu Val Ala Asn
        115                 120                 125

Lys Cys Ala Ala Glu Pro Trp Phe Gly Ile Glu Gln Glu Tyr Thr
    130                 135                 140

Phe Leu Asp Phe Asp Gly His Pro Leu Gly Trp Pro Lys Asn Gly Phe
145                 150                 155                 160

Pro Gly Pro Gln Gly Pro Tyr Tyr Cys Gly Val Gly Ala Asn Lys Val
                165                 170                 175

Tyr Ala Arg Asp Ile Val Asp Ala His Tyr Arg Ala Cys Leu Tyr Ala
            180                 185                 190

Gly Ile Lys Val Ser Gly Thr Asn Ala Glu Val Met Pro Ala Gln Trp
        195                 200                 205

Glu Phe Gln Val Gly Pro Cys Glu Gly Ile Ser Ile Gly Asp Asp Leu
    210                 215                 220

Trp Met Ala Arg Phe Leu Leu His Arg Ile Ser Glu Glu Phe Gly Ile
225                 230                 235                 240

Val Ser Thr Leu Asp Pro Lys Pro Met Pro Gly Asp Trp Asn Gly Ala
                245                 250                 255

Gly Ala His Thr Asn Val Ser Thr Lys Ala Met Arg Glu Asp Gly Gly
        260                 265                 270

Ile Arg Asp Ile Glu Lys Ala Val Ala Lys Leu Ser Lys Cys His Glu
    275                 280                 285

Arg His Ile Arg Ala Tyr Asp Pro Lys Gln Gly Gln Asp Asn Ala Arg
    290                 295                 300

Arg Leu Thr Gly Lys His Glu Thr Ser Ser Ile Asn Asp Phe Ser Ala
305                 310                 315                 320

Gly Val Ala Asn Arg Gly Cys Ser Ile Arg Ile Pro Arg Gly Val Asn
                325                 330                 335

Asp Asp Gly Lys Gly Tyr Phe Glu Asp Arg Arg Pro Ser Ser Asn Cys
            340                 345                 350

Asp Pro Tyr Ser Val Val Glu Ala Ile Leu Arg Thr Ile Cys Leu Asp
        355                 360                 365

Glu

<210> SEQ ID NO 8
<211> LENGTH: 1122
<212> TYPE: DNA
<213> ORGANISM: Homo sapiens

<400> SEQUENCE: 8

```
atgaccacct ccgcctccag ccacctgaac aagggcatca acaggtgta catgagcctg      60
ccccagggcg agaaggtgca ggccatgtac atctggatcg acggcaccgg cgagggactg    120
cggtgcaaga ccagaaccct ggactccgag cctaagtgcg tggaagaact gcccgagtgg    180
aacttcgacg gctcctccac cctgcagtcc gagggctcca actccgacat gtacctggtg    240
cctgccgcca tgttccggga cccttttccgg aaggacccca acaagctggt gctgtgcgag    300
gtgttcaagt acaacagacg gcctgccgag acaaacctgc ggcatacctg caagcggatc    360
atggacatgt gtccaaccag gcaccccttgg tttggcatgg aacaggagta cacccctgatg    420
ggcaccgacg gccacccctt cggctggcct tctaacggct ccctggccc caggggcccc    480
tactattgtg gcgtgggcgc cgaccggggcc tacggcagag atatcgtgga agcccactac    540
cgggcctgcc tgtacgccgg agtgaagatc gccggcacca cgccgaagt gatgcccgcc    600
cagtgggagt tccagatcgg cccttgcgag ggcatctcca tgggcgatca cctgtgggtg    660
gccccggttca tcctgcacag agtgtgcgag gacttcggcg tgatcgccac cttcgacccc    720
aagcccatcc ccggcaactg aacggcgct ggctgccaca ccaacttctc caccaaggcc    780
atgcgggaag agaacggcct gaagtacatc gaggaagcca tcgagaagct gtccaagcgg    840
caccagtacc acatcagagc ctacgaccct aagggcggcc tggacaacgc agaaggctg    900
accggctttc acgagacatc caacatcaac gacttctctg ccggcgtggc caacagatcc    960
gcctccatcc ggatccctag aaccgtgggc caggaaaaga agggctactt cgaggacaga   1020
cggcctccg ccaactgcga ccccttagc gtgaccgagg ccctgatccg gacctgcctg   1080
ctgaacgaga caggcgacga gcccttccag tacaagaact ga                    1122
```

<210> SEQ ID NO 9
<211> LENGTH: 1122
<212> TYPE: DNA
<213> ORGANISM: Canis lupus

<400> SEQUENCE: 9

```
atggccacct ccgcctccag ccacctgaac aagggcatca acaggtgta catgagcctg      60
```

| | |
|---|---|
| cccagggcg agaaggtgca ggccatgtac atctggatcg acggcaccgg cgagggactg | 120 |
| cggtgcaaga ccagaaccct ggactccgag cccaagggcg tggaagaact gcccgagtgg | 180 |
| aacttcgacg gctcctccac cttccagtcc gagggctcca actccgacat gtacctggtg | 240 |
| cctgccgcca tgttccggga cccttttccg aaggacccca caagctggt gttctgcgag | 300 |
| gtgttcaagt acaaccggaa gcccgccgag acaaacctgc ggcatacctg caagcggatc | 360 |
| atggacatgt gtccaaccag caccccttgg tttggcatgg aacaggagta caccctgatg | 420 |
| ggcaccgacg gccacccctt cggctggcct tctaacggct ccctggccc caggccccc | 480 |
| tactattgtg gcgtgggcgc cgacaaggcc tacggcagag acatcgtgga agcccactac | 540 |
| cgggcctgcc tgtacgccgg catcaagatc gctggcacca cgccgaagt gatgcccgcc | 600 |
| cagtgggagt tccagatcgg cccttgcgag ggcatcgaca tgggcgatca cctgtgggtg | 660 |
| gcccggttca tcctgcacag agtgtgcgag gacttcggcg tgatcgccac cttcgacccc | 720 |
| aagcccatcc ccggcaactg gaacggcgct ggctgccaca ccaacttctc caccaaggcc | 780 |
| atgcgggaag agaacggcct gaagtacatc gaggaatcca tcgagaagct gtccaagcgg | 840 |
| caccagtacc acatccgggc ctacgacccc aagggcggcc tggataacgc cagacggctg | 900 |
| accggcttcc acgagacatc caacatcaac gacttctctg ccggcgtggc caacagaggc | 960 |
| gcctccatcc ggatccccg gaccgtgggc caggaaaaga agggctactt cgaggacaga | 1020 |
| cggccctccg ccaactgcga cccctttagc gtgaccgagg ccctgatccg gacctgcctg | 1080 |
| ctgaacgaga caggcgacga gcccttccag tacaagaact ga | 1122 |

```
<210> SEQ ID NO 10
<211> LENGTH: 1122
<212> TYPE: DNA
<213> ORGANISM: Cricetulus griseus

<400> SEQUENCE: 10
```

| | |
|---|---|
| atggccacct cagcaagttc ccacttgaac aaaaacatca agcaaatgta cttgtgcctg | 60 |
| ccccagggtg agaaagtcca agccatgtat atctgggttg atggtactgg agaaggactg | 120 |
| cgctgcaaaa cccgcaccct ggactgtgag cccaagtgtg tagaagagtt acctgagtgg | 180 |
| aatttgatg gctctagtac cttcagtct gagggctcca acagtgacat gtatctcagc | 240 |
| cctgttgcca tgtttcggga ccccttccgc agagatccca caagctggt gttctgtgaa | 300 |
| gtttttcaagt acaaccggaa gcctgcagag accaatttaa ggcactcgtg taaacggata | 360 |
| atggacatgt gagcaacca gcacccctgg tttggaatgg aacaggagta tactctgatg | 420 |
| ggaacagatg ggcaccctt tggttggcct tccaatggct ttcctgggcc ccaaggtccg | 480 |
| tattactgtg gtgtgggcgc agacaaagcc tatggcaggg atatcgtgga ggctcactac | 540 |
| cgcgcctgct tgtatgctgg ggtcaagatt acaggaacaa atgctgaggt catgcctgcc | 600 |
| cagtgggaat tccaaatagg accctgtgaa ggaatccgca tggagatca tctctgggtg | 660 |
| gcccgtttca tcttgcatcg agtatgtgaa gactttgggg taatagcaac ctttgacccc | 720 |
| aagcccattc ctgggaactg gaatggtgca ggctgccata ccaactttag caccaaggcc | 780 |
| atgcgggagg agaatggtct gaagcacatc gaggaggcca tcgagaaact aagcaagcgg | 840 |
| caccggtacc acattcgagc ctacgatccc aagggggggcc tggacaatgc ccgtcgtctg | 900 |
| actgggttcc acgaaacgtc caacatcaac gacttttctg ctggtgtcgc caatcgcagt | 960 |
| gccagcatcc gcattccccg gactgtcggc caggagaaga aaggttactt tgaagaccgc | 1020 |

```
cgcccctctg ccaattgtga cccctttgca gtgacagaag ccatcgtccg cacatgcctt    1080
ctcaatgaga ctggcgacga gcccttccaa tacaaaaact aa                       1122
```

<210> SEQ ID NO 11
<211> LENGTH: 1113
<212> TYPE: DNA
<213> ORGANISM: Saccharomyces cerevisiae

<400> SEQUENCE: 11

```
atggccgagg cctccatcga aaagacccag atcctgcaga agtacctgga actggaccag    60
cggggcagaa tcattgccga gtacgtgtgg atcgacggca ccggcaacct gcggtctaag   120
ggccggaccc tgaagaagcg gatcacctcc atcgaccagc tgcccgagtg gaacttcgac   180
ggctcctcca ccaaccaggc ccctggccac gactccgaca tctacctgaa gcccgtggcc   240
tactaccccg accccttcag acggggcgac aacatcgtgg tgctggccgc ctgctacaac   300
aacgacggca cccccaacaa gttcaaccac cggcacgagg ccgccaagct gttcgccgcc   360
cacaaggacg aggaaatttg gttcggcctg aacaggagt acaccctgtt cgatatgtac   420
gacgacgtgt acggctggcc caagggcggc tatcctgccc ctcagggccc ctactactgt   480
ggcgtgggcg ctggcaaggt gtacgccaga gacatgatcg aggcccacta ccgggcctgc   540
ctgtacgccg gcctggaaat ctccggcatc aacgccgaag tgatgccctc ccagtgggag   600
ttccaggtgg accctgcac cggcatcgac atgggcgacc agctgtggat ggcccggtac   660
ttcctgcacc gggtggccga ggaattcggc atcaagatca gcttccaccc caagcccctg   720
aagggcgact ggaacggcgc tggatgccac gccaacgtgt ccaccaaaga gatgcggcag   780
cctggcggca ccaagtacat cgagcaggcc atcgagaagc tgtccaagcg gcacgccgag   840
cacatcaagc tgtacggctc cgacaacgac atgcggctga ccggcagaca cgagacagcc   900
tccatgaccg ccttctccag cggcgtggcc aaccggggct cctccatccg gatccctaga   960
agcgtggcca agagggcta cggctacttc gaggacagac ggcctgcctc caacatcgac  1020
ccctacctgg tgacaggcat catgtgcgag acagtgtgcg cgccatcga acgccgac    1080
atgaccaaag agttcgagag agtcctcc tga                                  1113
```

<210> SEQ ID NO 12
<211> LENGTH: 1122
<212> TYPE: DNA
<213> ORGANISM: Xenopus laevis

<400> SEQUENCE: 12

```
atggccacct ccgcctccgc ccagctgtcc aaggccatca gcagatgta cctggaactg     60
cctcagggcg acaaggtgca ggccatgtac atctggatcg acggcaccgg cgagggactg   120
cggtgcaaga ccagaaccct ggactccgag cccaagacca tcgaggacct gcccgagtgg   180
aacttcgacg gctcctccac ccaccagtcc gagggctcca actccgacat gtacctgatc   240
cccgtggcca tgttccggga ccctttccgg cgggacccca caagctggt gctgtgcgag   300
gtgctgaagt acaacagaaa gaccgccgag acaaacctgc ggcacacctg taaccagatc   360
atggacatgg tggaaacga gcacccttgg tttggcatgg aacaggagta caccctgctg   420
ggcatggacg gccaccctt cggctggcct tccaacggct ttcctggccc caggccc      480
tactattgcg gcgtgggcgc caacaaggcc tacggcagag acatcgtgga agcccactac   540
cgggcctgcc tgtacgccgg cgtgaagatc gccggcacca acgccgaagt gatgcccgcc   600
cagtgggagt tccagatcgg cacatgcgag ggcatcgaca tgggagacca cctgtggatc   660
```

```
gcccggttca tcctgcacag agtgtgcgag gacttcggca tcatcgtgtc cttcgacccc    720
aagcccatca ccggcaactg gaacggcgct ggctgccaca ccaacttctc caccaagtcc    780
atgcgggaag agggcggcct gaagcacatc gaggaatcca tcgagcggct gtccaagcgg    840
cacgagtacc acatcaggat gtacgacccc agaggcggca aggacaacgc cagacggctg    900
accggcttcc acgagacatc ctccatccac gagttctctg ctggcgtggc aacagaggc    960 gcctccatcc ggatcccaag actggtggga caggaaaaga agggctactt cgaggacaga   1020
cggccctccg ccaactgcga cccttacgct gtgaccgagg ccgtgatccg gacctgcctg   1080
ctgaacgaga caggcgacga gcccctggag tacaagaact ga                      1122
```

<210> SEQ ID NO 13
<211> LENGTH: 1065
<212> TYPE: DNA
<213> ORGANISM: Arabidopsis thaliana

<400> SEQUENCE: 13

```
atgtccctgc tgtccgacct ggtgaacctg aacctgaccg acgccaccgg caagatcatt    60
gccgagtaca tctggatcgg cggctccggc atggacatcc ggtctaaggc ccggacccctg   120 cctggccctg tgaccgaccc ctccaagctg cccaagtgga actacgacgg ctcctccacc   180
ggccaggccg ctggcgagga ctccgaagtg atcctgtatc acaggccat cttcaaggac    240 cctttccgga agggcaacaa catcctggtg atgtgcgacg cctacacccc tgccggcgac   300
cccatcccta ccaacaagcg gcacaacgcc gccaagatct ctcccacccc cgacgtggcc   360
aaagaggaac cttggtacgg catcgagcag gagtacaccc tgatgcagaa agacgtgaac   420
tggcccatcg gctggcccgt gggcggctat cctggccctc agggacctta ctactgcggc   480
gtgggcgccg acaaggccat cggcagagac atcgtggacg cccactacaa ggcctgcctg   540
tacgccggca tcggcatctc tggcatcaac ggcgaagtga tgcccggcca gtgggagttc   600
caggtgggac ccgtggaagg catctcctcc ggcgatcagg tgtgggtggc cagataccg   660 ctggaacgga tcaccgagat ctccggcgtg atcgtgtcct tcgacccaa gcccgtgccc   720 ggcgattgga atggcgctgg cgcccactgc aactactcca ccaagaccat gcggaacgac   780
ggcggcctgg aagtgatcaa gaaggctatc ggcaagctgc agctgaagca caaagagcat   840
atcgccgcct acggcgaggg caacgagcgg agactgaccg gcaagcacga cacagccgac   900
atcaacacct tcagctgggg cgtggccaac aggggcgctt ctgtgcgcgt gggccgggat   960
accgagaaag agggcaaggg ctacttcgag gacagacggc ctgcctccaa catggaccc   1020 tacgtggtga catccatgat cgccgagaca accatcctgg gctga                  1065
```

<210> SEQ ID NO 14
<211> LENGTH: 1110
<212> TYPE: DNA
<213> ORGANISM: Drosophila melanogaster

<400> SEQUENCE: 14

```
atgtccgccc ggatcctgga agattccccc aacgcccgga tcaacaagac catcctggac    60
agatacctga gcctgccact gcaggaaaac atcgtccagg ccacctacgt gtggatcgac   120
ggcacaggcg aggacctgcg gtgcaaggac cggaccctgg acttcatccc ccagtccccc   180
aaagaactgc ccgtgtggaa ctacgacggc tccagctgct accaggccga gggctccaac   240
tccgacacct acctgtaccc cgtggccatc tacaaggacc ccttcagacg gggcaacaac   300
```

```
atcctggtga tgtgcgacac ctacaagttc gatggcaccc ccaccgacac caacaagaga    360
aagacctgcc tggaagtggc caacaagtgt gccgccgagg aaccttggtt tggcatcgag    420
caggagtaca ccttcctgga cttcgacggc caccccctgg gctggcccaa gaatggcttt    480
cctggacccc agggcccta ctattgcggc gtgggcgcca acaaggtgta cgccagagac    540
atcgtggacg cccactaccg ggcctgcctg tacgccgaa tcaaggtgtc cggcaccaac    600
gccgaagtga tgcccgccca gtgggagttc caggtgggac cttgcgaggg catctccatc    660
ggcgacgacc tgtggatggc ccggttcctg ctgcaccgga tctccgagga attcggcatc    720
gtgtccaccc tggaccccaa gcccatgccc ggcgattgga atggcgctgg cgcccacacc    780
aacgtgtcca ccaaggccat gagagaggac ggcggcatcc gggacatcga gaaggccgtg    840
gccaagctgt ccaagtgcca cgagcggcac atccgggcct acgaccctaa gcagggccag    900
gacaacgcca gacggctgac cggcaagcac gagacatcct ccatcaacga cttctctgcc    960
ggcgtggcca accggggctg ctccatcaga atccctcggg gcgtgaacga cgacggcaag    1020
ggctacttcg aggacagacg gccctcctcc aactgcgacc cttactccgt ggtggaagcc    1080
atcctgcgga ccatctgcct ggacgagtga                                     1110
```